(12) United States Patent
Fernandez de Castro et al.

(10) Patent No.: US 8,263,098 B2
(45) Date of Patent: *Sep. 11, 2012

(54) HIGH ALCOHOL CONTENT FOAMING COMPOSITIONS WITH SILICONE-BASED SURFACTANTS

(75) Inventors: Maria Teresa Fernandez de Castro, Brantford (CA); Bruce Michael Koivisto, Willsonville (CA); Francisco Munoz, Brantford (CA)

(73) Assignee: Deb Worldwide Healthcare Inc., Ontario (CA)

( * ) Notice: Subject to any disclaimer, the term of this patent is extended or adjusted under 35 U.S.C. 154(b) by 1407 days.

This patent is subject to a terminal disclaimer.

(21) Appl. No.: 10/591,243

(22) PCT Filed: Mar. 7, 2006

(86) PCT No.: PCT/CA2006/000320
§ 371 (c)(1),
(2), (4) Date: Aug. 31, 2006

(87) PCT Pub. No.: WO2006/094387
PCT Pub. Date: Sep. 14, 2006

(65) Prior Publication Data
US 2007/0179207 A1 Aug. 2, 2007

Related U.S. Application Data

(60) Provisional application No. 60/658,580, filed on Mar. 7, 2005.

(51) Int. Cl.
| A01N 25/00 | (2006.01) |
| A61K 31/74 | (2006.01) |
| A61K 51/00 | (2006.01) |
| A61M 36/14 | (2006.01) |

(52) U.S. Cl. ............. 424/405; 424/1.65; 424/78.07
(58) Field of Classification Search .......... 424/405, 424/1.65, 78.07
See application file for complete search history.

(56) References Cited

U.S. PATENT DOCUMENTS

| 2,054,989 A | 9/1936 | Moore |
| 2,559,749 A | 7/1951 | Benning |
| 2,597,702 A | 5/1952 | Benning |
| 2,599,140 A | 6/1952 | Taub |
| 2,855,367 A | 10/1958 | Buck |
| 3,131,152 A | 4/1964 | Klausner |
| 3,131,153 A | 4/1964 | Klausner |
| 3,395,214 A | 7/1968 | Mummert |
| 3,708,435 A | 1/1973 | Starkman |
| 3,709,437 A | 1/1973 | Wright |
| 3,770,648 A | 11/1973 | Mackles |
| 3,787,566 A | 1/1974 | Gauvreau et al. |
| 3,824,303 A | 7/1974 | Lanzet |
| 3,928,558 A | 12/1975 | Cheesman et al. |
| 3,962,150 A | 6/1976 | Viola |
| 3,963,507 A | 6/1976 | Kuramoto et al. |
| 4,018,364 A | 4/1977 | Wright |
| 4,086,178 A | 4/1978 | Walker |
| 4,220,665 A | 9/1980 | Klein |
| 4,225,456 A | 9/1980 | Schmidt et al. |
| 4,311,695 A | 1/1982 | Starch |
| 4,313,978 A | 2/1982 | Stevens |
| 4,336,151 A | 6/1982 | Like et al. |
| 4,440,652 A | 4/1984 | Hunter |
| 4,440,653 A * | 4/1984 | Briscoe et al. ............ 507/202 |
| 4,454,060 A | 6/1984 | Lai et al. |
| 4,478,853 A | 10/1984 | Chaussee |
| 4,511,486 A | 4/1985 | Shah |
| 4,559,226 A | 12/1985 | Fogel et al. |
| 4,567,038 A | 1/1986 | Ciaudelli et al. |
| 4,584,189 A | 4/1986 | Leipold |
| 4,613,592 A | 9/1986 | Benzoni |
| 4,714,568 A | 12/1987 | Hurnik et al. |
| 4,772,592 A | 9/1988 | Benzoni |

(Continued)

FOREIGN PATENT DOCUMENTS

| AU | 2003203452 B1 | 10/2004 |
| CA | 2 323 780 A1 | 4/2001 |
| CA | 2534692 | 2/2005 |
| CA | 2 587 086 | 4/2006 |
| DE | 28 52 593 | 6/1979 |
| DE | 3306593 A1 | 2/1983 |
| DE | 19523320 | 1/1997 |
| DE | 695 12 841 T2 | 5/2000 |
| DE | 10 2004 050 211 A1 | 4/2006 |
| EP | 0 160 051 | 11/1985 |

(Continued)

OTHER PUBLICATIONS

U.S. Appl. No. 12/659,063, filed Feb. 2011, Koivisto et al.*
U.S. Appl. No. 11/520,819, filed Sep. 2011, Castro et al.*
U.S. Appl. No. 11/806,767, filed Jun. 2011, Castro et al.*
Degussa, Creating Essentials, "Goldschmidt Personal Care", Catalogue of Products, May 2003.

(Continued)

Primary Examiner — Mina Haghighatian
Assistant Examiner — Mei-Ping Chui
(74) Attorney, Agent, or Firm — Neal, Gerber & Eisenberg LLP

(57) ABSTRACT

This invention relates to a "high lower alcohol content" (>40% v/v of a $C_{1-4}$ alcohol) liquid composition able to be dispensed as a stable foam with the use of non-propellant foam dispensing devices from non-pressurized containers. The liquid compositions comprise an alcohol, $C_{1-4}$ (>40% v/v), a silicone-based surfactant of at least 0.001% by weight to prepare a foamable composition, 0-10% w/w of additional minor components added to obtain the desired performance (a foamable composition), and the balance being purified water. The compositions may include emulsifier-emollients and mosturizers, secondary surfactants, foam stabilizers, fragrances, antimicrobial agents, other type of medicinal ingredients, and the like ingredients or additives or combinations thereof commonly added to alcohol gels or foams, aerosol compositions or to toiletries, cosmetics, pharmaceuticals and the like.

25 Claims, No Drawings

U.S. PATENT DOCUMENTS

| | | | |
|---|---|---|---|
| 4,826,828 A | 5/1989 | Wilmott et al. | |
| 4,839,166 A | 6/1989 | Grollier et al. | |
| 4,839,167 A | 6/1989 | Yamamoto et al. | |
| 4,857,302 A | 8/1989 | Decker et al. | |
| 4,897,262 A | 1/1990 | Nandagiri et al. | |
| 4,906,459 A | 3/1990 | Cobb et al. | |
| 4,915,934 A | 4/1990 | Tomlinson | |
| 4,919,837 A | 4/1990 | Glack | |
| 4,956,170 A | 9/1990 | Lee | |
| 4,956,173 A | 9/1990 | Le Fur et al. | |
| 4,981,678 A | 1/1991 | Tomlinson | |
| 4,983,377 A | 1/1991 | Murphy et al. | |
| 4,986,922 A | 1/1991 | Snow et al. | |
| 4,988,453 A | 1/1991 | Chambers | |
| 5,015,228 A | 5/1991 | Columbus et al. | |
| 5,043,088 A | 8/1991 | Falla | |
| 5,047,249 A | 9/1991 | Rothman et al. | |
| 5,073,371 A | 12/1991 | Turner et al. | |
| 5,100,658 A | 3/1992 | Bolich, Jr. et al. | |
| 5,104,646 A | 4/1992 | Bolich, Jr. et al. | |
| 5,122,541 A | 6/1992 | Eggensperger et al. | |
| 5,128,123 A | 7/1992 | Brewster et al. | |
| 5,167,950 A | 12/1992 | Lins | |
| 5,180,584 A | 1/1993 | Sebag et al. | |
| 5,204,099 A | 4/1993 | Barbier et al. | |
| D338,585 S | 8/1993 | Bell | |
| 5,232,691 A | 8/1993 | Lemole | |
| 5,256,401 A | 10/1993 | Duckenfield | |
| 5,265,772 A | 11/1993 | Bartasevich | |
| 5,266,598 A | 11/1993 | Ninomiya et al. | |
| D343,751 S | 2/1994 | Bell | |
| 5,288,486 A | 2/1994 | White | |
| 5,290,555 A | 3/1994 | Guthauser et al. | |
| D346,332 S | 4/1994 | Kanfer | |
| 5,300,284 A | 4/1994 | Wiechers et al. | |
| 5,314,684 A | 5/1994 | Horoschak et al. | |
| 5,336,497 A | 8/1994 | Guerrero et al. | |
| 5,352,437 A | 10/1994 | Nakagawa et al. | |
| 5,362,484 A | 11/1994 | Wood et al. | |
| 5,370,267 A | 12/1994 | Schroeder | |
| 5,415,811 A | 5/1995 | Wile | |
| 5,439,682 A * | 8/1995 | Wivell et al. | 424/401 |
| 5,441,178 A | 8/1995 | Wysocki | |
| 5,443,236 A | 8/1995 | Bell | |
| 5,445,288 A | 8/1995 | Banks | |
| 5,449,137 A | 9/1995 | Bell | |
| 5,462,688 A | 10/1995 | Lippman | |
| D365,509 S | 12/1995 | Bell | |
| D365,518 S | 12/1995 | Wysocki | |
| D365,755 S | 1/1996 | Kanfer | |
| 5,484,597 A | 1/1996 | Slavtcheff et al. | |
| 5,494,533 A | 2/1996 | Woodin, Jr. et al. | |
| 5,523,014 A | 6/1996 | Dolan | |
| 5,547,662 A | 8/1996 | Khan et al. | |
| 5,549,888 A | 8/1996 | Venkateswaran | |
| 5,558,453 A | 9/1996 | Bell | |
| 5,567,428 A | 10/1996 | Hughes | |
| 5,587,358 A | 12/1996 | Sukigara | |
| 5,607,980 A | 3/1997 | McAtee et al. | |
| 5,612,324 A | 3/1997 | Guang Lin et al. | |
| 5,625,659 A | 4/1997 | Sears | |
| 5,626,853 A | 5/1997 | Bara et al. | |
| 5,629,006 A | 5/1997 | Hoang | |
| 5,635,462 A | 6/1997 | Fendler | |
| 5,635,469 A | 6/1997 | Fowler et al. | |
| D383,001 S | 9/1997 | Bell | |
| 5,662,893 A | 9/1997 | George et al. | |
| 5,665,332 A | 9/1997 | Mundschenk et al. | |
| D385,795 S | 11/1997 | Wysocki | |
| 5,690,921 A | 11/1997 | Lang et al. | |
| 5,693,255 A | 12/1997 | Okamoto et al. | |
| 5,718,353 A | 2/1998 | Kanfer | |
| 5,719,113 A | 2/1998 | Fendler | |
| D392,136 S | 3/1998 | Ross | |
| 5,733,535 A | 3/1998 | Hollingshead et al. | |
| 5,756,077 A | 5/1998 | Syed et al. | |
| 5,767,161 A | 6/1998 | Stroppolo et al. | |
| 5,776,430 A | 7/1998 | Osborne et al. | |
| 5,789,371 A | 8/1998 | Tracy et al. | |
| 5,824,320 A | 10/1998 | Rouillard et al. | |
| D400,799 S | 11/1998 | Bell | |
| 5,834,516 A | 11/1998 | O'Lenick, Jr. | |
| 5,843,881 A * | 12/1998 | Dubois et al. | 512/1 |
| 5,856,347 A | 1/1999 | Hashiguchi et al. | |
| 5,863,884 A | 1/1999 | Lafreniere | |
| 5,902,778 A | 5/1999 | Hartmann et al. | |
| 5,906,808 A | 5/1999 | Osborne | |
| D411,456 S | 6/1999 | Mast | |
| 5,908,619 A | 6/1999 | Scholz | |
| 5,919,439 A | 7/1999 | Torgerson et al. | 424/70.122 |
| 5,922,663 A | 7/1999 | Gabriel et al. | |
| 5,928,993 A | 7/1999 | Johansson | |
| 5,935,587 A | 8/1999 | Cauwet et al. | |
| 5,944,227 A | 8/1999 | Schroeder et al. | |
| 5,951,993 A | 9/1999 | Scholz et al. | |
| 5,952,290 A | 9/1999 | Li et al. | |
| 5,955,408 A | 9/1999 | Kaiser | |
| 5,955,416 A | 9/1999 | Baillely et al. | |
| D415,343 S | 10/1999 | Maddox | |
| 5,972,356 A | 10/1999 | Peffly et al. | |
| D416,417 S | 11/1999 | Ross | |
| 5,980,876 A | 11/1999 | Peffly | 424/70.12 |
| 5,996,851 A | 12/1999 | Dolan | |
| D418,708 S | 1/2000 | Kanfer | |
| 6,019,997 A | 2/2000 | Scholz et al. | |
| 6,022,551 A | 2/2000 | Jampani et al. | |
| 6,039,965 A | 3/2000 | Donian et al. | |
| D422,828 S | 4/2000 | Kanfer | |
| 6,065,639 A | 5/2000 | Maddox | |
| 6,086,856 A | 7/2000 | Saferstein et al. | |
| 6,090,395 A | 7/2000 | Asmus | |
| 6,117,440 A | 9/2000 | Suh | |
| 6,130,253 A | 10/2000 | Franklin et al. | |
| 6,183,766 B1 | 2/2001 | Sine et al. | |
| 6,217,885 B1 | 4/2001 | Röder et al. | |
| 6,255,265 B1 | 7/2001 | Van Gunst | |
| 6,262,128 B1 | 7/2001 | Stern et al. | |
| 6,265,363 B1 | 7/2001 | Viscovitz | |
| 6,267,976 B1 | 7/2001 | Barnhart | |
| 6,274,124 B1 | 8/2001 | Vollhardt | |
| 6,277,359 B1 | 8/2001 | Raths et al. | |
| 6,319,958 B1 | 11/2001 | Johnson et al. | |
| 6,333,039 B1 | 12/2001 | Fendler et al. | |
| 6,339,165 B1 | 1/2002 | Endo et al. | |
| 6,342,470 B1 | 1/2002 | Aronson | |
| 6,352,701 B1 | 3/2002 | Scholz et al. | |
| 6,358,914 B1 | 3/2002 | Gabriel et al. | |
| 6,376,438 B1 | 4/2002 | Rosenberger et al. | |
| 6,383,505 B1 | 5/2002 | Kaiser | |
| 6,383,997 B1 | 5/2002 | McManus | |
| 6,410,005 B1 | 6/2002 | Galleguillos et al. | 424/70.16 |
| 6,423,329 B1 | 7/2002 | Sine et al. | |
| 6,462,002 B2 | 10/2002 | Saxena | |
| 6,471,983 B1 | 10/2002 | Veeger et al. | |
| 6,472,356 B2 | 10/2002 | Narula et al. | |
| 6,479,442 B1 | 11/2002 | Berube | |
| 6,489,275 B1 | 12/2002 | Veeger et al. | |
| 6,491,840 B1 | 12/2002 | Frankenbach et al. | |
| 6,497,864 B1 | 12/2002 | Samain et al. | |
| 6,518,228 B1 | 2/2003 | Jorgensen | |
| 6,524,494 B2 | 2/2003 | Hart et al. | |
| 6,524,594 B1 | 2/2003 | Santora | |
| 6,528,544 B2 | 3/2003 | Stern et al. | |
| 6,534,069 B1 | 3/2003 | Asmus et al. | |
| 6,537,952 B2 | 3/2003 | Hayward et al. | |
| 6,551,605 B2 | 4/2003 | Bondo | |
| 6,555,508 B1 | 4/2003 | Paul et al. | |
| 6,562,360 B2 | 5/2003 | Scholz | |
| 6,582,711 B1 | 6/2003 | Asmus et al. | |
| 6,592,880 B1 | 7/2003 | Jager | |
| 6,610,315 B2 | 8/2003 | Scholz | |
| 6,617,294 B2 | 9/2003 | Narula et al. | |
| 6,623,744 B2 | 9/2003 | Asmus | |
| 6,638,527 B2 | 10/2003 | Gott | |
| 6,641,825 B2 | 11/2003 | Scholz | |
| 6,664,256 B1 | 12/2003 | Oohkuchi et al. | |
| 6,664,356 B1 | 12/2003 | Shih | |

| | | |
|---|---|---|
| 6,666,217 B2 | 12/2003 | Elsner |
| 6,685,952 B1 | 2/2004 | Ma et al. |
| 6,689,593 B2 | 2/2004 | Millis |
| 6,696,397 B2 | 2/2004 | Staats |
| 6,703,007 B2 | 3/2004 | Glenn, Jr. .................... 424/70.1 |
| 6,706,675 B1 | 3/2004 | Demson |
| 6,709,647 B2 | 3/2004 | Bhakoo |
| 6,710,022 B1 | 3/2004 | Kwetkat et al. |
| 6,723,689 B1 | 4/2004 | Hoang |
| 6,730,621 B2 | 5/2004 | Gott |
| 6,759,376 B2 | 7/2004 | Zhang |
| 6,762,158 B2 | 7/2004 | Lukenbach |
| 6,777,384 B2 | 8/2004 | Raths et al. |
| 6,780,826 B2 | 8/2004 | Zhang |
| 6,794,345 B2 | 9/2004 | Elsner et al. |
| 6,797,687 B2 | 9/2004 | Kischkel et al. |
| 6,805,141 B2 | 10/2004 | Elsner et al. |
| 6,815,410 B2 | 11/2004 | Boutique |
| 6,818,603 B2 | 11/2004 | Aleles |
| 6,846,846 B2 | 1/2005 | Modak et al. |
| 6,875,539 B2 | 4/2005 | Ophardt |
| 6,884,763 B2 | 4/2005 | Willard |
| 6,946,120 B2 | 9/2005 | Wai-Chiu et al. |
| 6,977,082 B2 | 12/2005 | Seitz, Jr. et al. |
| 7,081,246 B2 | 7/2006 | Asmus et al. |
| 7,141,237 B2 | 11/2006 | Abram et al. |
| 7,163,916 B2 | 1/2007 | Allef et al. |
| 7,164,041 B1 | 1/2007 | Moore et al. |
| 7,166,435 B2 | 1/2007 | Rosenbloom |
| 7,199,090 B2 * | 4/2007 | Koivisto et al. ................ 510/138 |
| 7,241,452 B2 | 7/2007 | Veeger et al. |
| 7,297,675 B2 | 11/2007 | Allef et al. |
| 7,393,817 B2 | 7/2008 | Kwetkat et al. |
| 7,530,477 B2 | 5/2009 | Ophardt |
| 7,547,732 B2 | 6/2009 | Moore et al. |
| 7,566,460 B2 | 7/2009 | Asmus et al. |
| 7,597,898 B2 | 10/2009 | Birkel et al. |
| 7,651,990 B2 | 1/2010 | Asmus |
| 7,670,615 B2 | 3/2010 | Veeger |
| 7,683,018 B2 * | 3/2010 | Koivisto et al. ................ 510/138 |
| 7,723,279 B2 | 5/2010 | Lestage et al. |
| 7,790,663 B2 | 9/2010 | Lestage et al. |
| 7,803,390 B2 | 9/2010 | Asmus et al. |
| 7,842,725 B2 | 11/2010 | Wegner et al. |
| 7,850,048 B2 | 12/2010 | Arminak |
| 8,058,315 B2 | 11/2011 | Wegner et al. |
| 2002/0022660 A1 | 2/2002 | Jampani |
| 2002/0028187 A1 | 3/2002 | Nekludoff et al. |
| 2002/0039562 A1 | 4/2002 | Kobayashi et al. |
| 2002/0098159 A1 | 7/2002 | Wei et al. |
| 2002/0106399 A1 | 8/2002 | Durden |
| 2002/0108640 A1 | 8/2002 | Barger et al. |
| 2002/0127253 A1 | 9/2002 | Scholz et al. |
| 2002/0142018 A1 | 10/2002 | Scholz et al. |
| 2002/0151446 A1 | 10/2002 | Piterski et al. |
| 2002/0160029 A1 | 10/2002 | Asmus et al. |
| 2002/0160924 A1 | 10/2002 | Bertrem et al. ................ 510/189 |
| 2002/0177535 A1 | 11/2002 | Piterski et al. |
| 2002/0187908 A1 | 12/2002 | Gagilardi et al. ............ 510/278 |
| 2003/0134761 A1 | 7/2003 | Sebillotte-Arnaud et al. |
| 2003/0203824 A1 | 10/2003 | Staats |
| 2003/0211066 A1 | 11/2003 | Scholz et al. |
| 2003/0213542 A1 | 11/2003 | Kobayashi et al. |
| 2003/0215418 A1 | 11/2003 | Asmus et al. |
| 2003/0235550 A1 | 12/2003 | Pan et al. |
| 2004/0001797 A1 | 1/2004 | Saud et al. |
| 2004/0071748 A1 | 4/2004 | Asmus et al. |
| 2004/0072700 A1 | 4/2004 | Gupta |
| 2004/0102429 A1 | 5/2004 | Modak et al. |
| 2004/0167195 A1 * | 8/2004 | Muller .......................... 514/400 |
| 2004/0170592 A1 | 9/2004 | Veeger et al. |
| 2004/0191195 A1 | 9/2004 | Collins et al. |
| 2004/0191274 A1 | 9/2004 | Grayson et al. |
| 2004/0219227 A1 | 11/2004 | Modak et al. |
| 2004/0241099 A1 | 12/2004 | Popp et al. |
| 2004/0247685 A1 | 12/2004 | Modak et al. |
| 2004/0265240 A1 | 12/2004 | Tamarkin et al. |
| 2005/0003990 A1 | 1/2005 | Smith et al. |
| 2005/0031580 A1 | 2/2005 | Allef et al. |
| 2005/0031653 A1 | 2/2005 | Kwetkat et al. |
| 2005/0031847 A1 * | 2/2005 | Martens et al. ............ 428/321.5 |
| 2005/0063925 A1 | 3/2005 | Candau et al. |
| 2005/0109981 A1 | 5/2005 | Tucker et al. |
| 2005/0129626 A1 | 6/2005 | Koivisto et al. |
| 2005/0152931 A1 | 7/2005 | SaNogueira et al. |
| 2005/0222001 A1 | 10/2005 | Baumeister et al. |
| 2005/0226838 A1 | 10/2005 | Krause et al. |
| 2005/0277574 A1 | 12/2005 | Niedbala et al. |
| 2006/0018847 A1 | 1/2006 | Kroepke et al. |
| 2006/0104911 A1 | 5/2006 | Novak |
| 2006/0104919 A1 | 5/2006 | Novak ............................ 424/47 |
| 2006/0110416 A1 | 5/2006 | Ryles et al. |
| 2006/0121071 A1 | 6/2006 | Asmus et al. |
| 2006/0165627 A1 | 7/2006 | Allef et al. |
| 2006/0182690 A1 | 8/2006 | Veeger |
| 2006/0198859 A1 | 9/2006 | Allef et al. |
| 2006/0204468 A1 | 9/2006 | Allef et al. |
| 2006/0257334 A1 | 11/2006 | Dahms et al. |
| 2006/0263396 A1 | 11/2006 | Asmus et al. |
| 2006/0275226 A1 | 12/2006 | Dahms et al. |
| 2006/0281663 A1 | 12/2006 | Asmus |
| 2007/0027055 A1 | 2/2007 | Koivisto et al. |
| 2007/0041927 A1 | 2/2007 | Blaeser et al. |
| 2007/0065383 A1 | 3/2007 | Fernandez de Castro et al. |
| 2007/0092470 A1 | 4/2007 | Allef et al. |
| 2007/0141007 A1 | 6/2007 | Glynn, Jr. et al. |
| 2007/0148101 A1 | 6/2007 | Snyder et al. |
| 2007/0179207 A1 | 8/2007 | Fernandez de Castro et al. |
| 2007/0258911 A1 | 11/2007 | Fernandez de Castro et al. |
| 2008/0051312 A1 | 2/2008 | Lestage et al. |
| 2008/0108704 A1 | 5/2008 | Asmus et al. |
| 2008/0145320 A1 | 6/2008 | Wenk et al. |
| 2008/0178899 A1 | 7/2008 | Moenks et al. |
| 2008/0207767 A1 | 8/2008 | Dobos |
| 2008/0293825 A1 | 11/2008 | Littau et al. |
| 2008/0305056 A1 | 12/2008 | Jenni et al. |
| 2009/0054521 A1 | 2/2009 | Herrwerth et al. |
| 2009/0098067 A1 | 4/2009 | Seidling et al. |
| 2009/0326076 A1 | 12/2009 | Asmus |
| 2010/0022660 A1 | 1/2010 | Wegner et al. |
| 2010/0069505 A1 | 3/2010 | Veeger et al. |
| 2010/0160453 A1 | 6/2010 | Koivisto et al. |
| 2010/0187263 A1 | 7/2010 | Lestage et al. |
| 2010/0234475 A1 | 9/2010 | Wegner et al. |
| 2010/0327013 A1 | 12/2010 | Asmus |
| 2010/0331411 A1 | 12/2010 | Asmus |
| 2011/0104079 A1 | 5/2011 | Snyder et al. |
| 2011/0110869 A1 | 5/2011 | Scholtz et al. |
| 2011/0201693 A1 | 8/2011 | Littau |
| 2011/0319364 A1 | 12/2011 | Wegner et al. |

FOREIGN PATENT DOCUMENTS

| | | |
|---|---|---|
| EP | 0 213 527 | 3/1987 |
| EP | 0 117 889 | 11/1987 |
| EP | 0 260 641 | 3/1988 |
| EP | 0 384 126 | 8/1990 |
| EP | 0 689 767 | 1/1996 |
| EP | 0882446 | 12/1998 |
| EP | 0 990 412 | 4/2000 |
| EP | 1 118 655 | 7/2001 |
| EP | 1 584 323 | 10/2005 |
| EP | 1 893 167 A1 | 3/2008 |
| EP | 1811013 B1 | 8/2009 |
| GB | 2 010 874 | 7/1979 |
| JP | 11349418 | 12/1999 |
| JP | 06279268 | 10/2006 |
| JP | 07285808 A | 11/2007 |
| WO | WO 85/01876 * | 5/1985 |
| WO | 93/00089 | 1/1993 |
| WO | 93/07250 | 4/1993 |
| WO | 95/01384 | 1/1995 |
| WO | 95/03772 | 2/1995 |
| WO | 97/00667 | 1/1997 |
| WO | 97/00667 A1 | 1/1997 |
| WO | 97/00668 | 1/1997 |
| WO | 99/20250 | 4/1999 |
| WO | 00/06107 | 2/2000 |
| WO | 00/47183 | 8/2000 |

| WO | 2002062936 A1 | 8/2002 |
| WO | 03/028671 | 4/2003 |
| WO | 03/034994 | 5/2003 |
| WO | 03/053388 | 7/2003 |
| WO | 2004000016 A2 | 12/2003 |
| WO | 2005/030917 | 9/2004 |
| WO | WO 2005030917 | 4/2005 |
| WO | 2005-051341 | 6/2005 |
| WO | 2005/123012 | 12/2005 |
| WO | 2006/042588 | 4/2006 |
| WO | 2006/066888 | 6/2006 |
| WO | WO 2006/094387 | 9/2006 |
| WO | 2006138111 | 12/2006 |
| WO | 2007095008 | 8/2007 |
| WO | 2008/132621 A1 | 11/2008 |
| WO | 2010/010475 | 1/2010 |

OTHER PUBLICATIONS

Dewar et al., Effectiveness of Septisol Antiseptic Foam as a Surgical Scrub Agent, Applied Microbiology, Oct. 1973, vol. 26, No. 4, p. 544-549.
Beck, W, Alcohol foam for hand disinfection, AORN Journal, Dec. 1980, vol. 32, No. 6, p. 1087-1088.
3M Fluorad Well Stimulation Additive FC-742 Foamer for Aqueous/Alcoholic Fluids, 3M 1987, 6 pages.
Sandra J. Pfaff, Letters to the Editor, Alcohol Foam Use Questioned, AORN Journal, Dec. 1989, vol. 50, No. 6, 1 page.
3M Product Information Well Stimulation Additive FC-742, Foamer for Aqueous/Alcoholic Fluids, 1994, 4 pages.
Zonyl FSP fluorosurfactant, Technical Information, DuPont, 1998, 2 pages.
Rosen et al., Industrial Utilization of Surfactants; Principles and Practice, AOCS Press, 2000, 4 pages.
Pabon et al., Fluorinated surfactants: synthesis, properties effluent treatment, J. Fluorine Chem. 114 (2002), p. 149-156.
U.S. Appl. No. 60/506,172, filed Sep. 29, 2003, Koivisto.
U.S. Appl. No. 60/591,601, filed Jul. 28, 2004, Koivisto.
Product Information Sheet, Mackanate DC-50, McIntyre Group Ltd., 1 page.
Product Information Sheet, Dow Corning 2501, Cosmetic Wax, 4 sheets.
Product Description, GE Silicones, SF1202, Dec. 22, 2004, 6 sheets.
Product Description, GE Silicones, SF 1388, Dec. 22, 2004, 2 sheets.
Product Information, DOW Corning, Sylgard 309 Silicone Surfactant, 3 sheets.
Product Description, GE Advance Materials Silicones, SF1388, 2 sheets, Jan. 5, 2005.
Defendant BETCO, Corporation's Initial Disclosures Pursuant to Fed. R. Civ. P. 26(a) (1), *DEB Worldwide Healthcare, Inc.* v. *BETCO, Corp.*, Case No. 3:08-cv-00052-bbc, US District Court for the Western District of Wisconsin, Apr. 2, 2008.
First Amended Complaint, *DEB Worldwide Healthcare, Inc.* v. *BETCO, Corp.*, Case No. 3:08-cv-00052-bbc, US District Court for the Western District of Wisconsin, document #21, Apr. 21, 2008.
Complaint, *DEB Worldwide Healthcare, Inc.* v. *BETCO, Corp.*, Case No. 3:08-cv-00052-bbc, US District Court for the Western District of Wisconsin, document #1, Jan. 22, 2008.
U.S. Office Action mailed Jun. 28, 2010 for U.S. Appl. No. 11/438,664.
Preliminary Amendment dated Jul. 24, 2008 in U.S. Appl. No. 12/179,410 (Publication No. 2008-0293825 published on Nov. 27, 2008).
International Search Report for International Application No. PCT/US2006/021904 mailed Oct. 24, 2006.
Notice of Allowance dated Jul. 20, 2010 for U.S. Appl. No. 12/179,382.
Supplemental Response and Amendment filed on Aug. 13, 2010 for U.S. Appl. No. 12/032,083.
Request for Continued Examination filed on Jul. 6, 2010 for U.S. Appl. No. 12/032,083.
Advisory Action Communication mailed Jun. 29, 2010 for U.S. Appl. No. 12/032,083.
U.S. Office Action mailed Aug. 3, 2010 for U.S. Appl. No. 11/075,287.
U.S. Office Action mailed Aug. 3, 2010 for U.S. Appl. No. 11/369,381.
Response and Amendment after Final Office Action filed on Jun. 2, 2010 for U.S. Appl. No. 12/032,083.
Communication of Notices of Opposition to a European Patent (EP 1 811 013) filed by Ecolab, Inc., 3M Innovative Properties Company and DEB Worldwide Healthcare Inc. against Gojo Industries dated Jun. 16, 2010.
Affidavit of Bruce Michael Koivisto signed and dated on May 17, 2010.
"Dow Corning@ 190 Fluid" product information. Dow Corning, Midland, MI Feb. 24, 2010, Ref. No. 22-1616E-01 (3 pages).
Printout of http://www.rexamairspray.com/products-foampump.php Oct. 5, 2010 (2 pages).
Notice of Opposition to a European Patent (EP 1 811 013) filed by 3M Innovative Properties Company against Gojo Industries dated May 12, 2010.
Notice of Opposition to a European Patent (EP 1 811 013) filed by Ecolab, Inc. against Gojo Industries dated May 6, 2010.
Affidavit of Caroline Fellows dated May 10, 2010.
Technical Information for LUVIQUAT® PQ 11, BASF, May 1997 (3 pages).
Response and Amendment dated Apr. 7, 2010 for U.S. Appl. No. 11/438,664.
Declaration of Amanda J. Copeland dated Apr. 7, 2010.
Notice of Opposition to a European Patent (EP 1 811 013) filed by DEB Worldwide Healthcare Inc. against Gojo Industries dated May 12, 2010.
Complaint for Correction of Inventorship of Patent; Case 1:10-CV-00266-GMS, filed Apr. 2, 2010 in the United States District Court for the District of Delaware.
Worldwide Healthcare, Inc., "Material Safety Data Sheet", Jan. 24, 2007.
U.S. Office Action mailed Apr. 30, 2007 for U.S. Appl. No. 11/799,042.
U.S. Office Action mailed Feb. 24, 2010 for U.S. Appl. No. 12/659,063.
Amendment and Response filed Oct. 31, 2007 in U.S. Appl. No. 11/340,778.
Amendment and Response filed Oct. 31, 2007 in U.S. Appl. No. 10/400,597.
Amendment and Request for Reconsideration filed Jun. 2, 2008 in U.S. Appl. No. 11/312,559.
Interview Summary mailed Apr. 23, 2008 in U.S. Appl. No. 11/312,559.
Non-final rejection mailed Feb. 20, 2008 in U.S. Appl. No. 11/312,559.
Amendment and Request for Reconsideration filed Jun. 22, 2007 in U.S. Appl. No. 11/312,559.
Non-final Rejection mailed Feb. 22, 2007 in U.S. Appl. No. 11/312,559.
S.C. Crema et al., "Foaming of Anhydrous Methanol for Well Stimulation", Society of Petroleum Engineers, SPE 13565, (1985).
Paul A. Sanders, "Aqueous Alcohol Aerosol Foams", Drug & Cosmetic Industry, XP000960450, vol. 99, No. 2, 1966, pp. 56, 58, 60, 142, 143, 146-154.
Non-Final Rejection mailed Jan. 3, 2006 in U.S. Appl. No. 10/992,494.
Amendment and Response filed Jul. 3, 2006 in U.S. Appl. No. 10/992,494.
Non-Final Rejection mailed Sep. 26, 2006 in U.S. Appl. No. 10/992,494.
Amendment and Response and RCE filed Mar. 26, 2007 in U.S. Appl. No. 10/992,494.
Final Rejection mailed Apr. 9, 2007 in U.S. Appl. No. 10/992,494.
Final Rejection mailed May 7, 2007 in U.S. Appl. No. 11/048,031.
Non-Final rejection mailed May 11, 2006 in U.S. Appl. No. 11/048,031.
Amendment and Response filed Aug. 11, 2006 in U.S. Appl. No. 11/048,031.
Final Rejection mailed Feb. 11, 2008 in U.S. Appl. No. 11/048,040.

Amendment and Response filed Nov. 29, 2007 in U.S. Appl. No. 11/048,040.
Notice of Non-Compliant Amendment mailed Oct. 29, 2007 in U.S. Appl. No. 11/048,040.
Amendment and Response filed Oct. 16, 2007 in U.S. Appl. No. 11/048,040.
Non-final Rejection mailed Jul. 16, 2007 in U.S. Appl. No. 11/048,040.
Amendment and Response filed Jun. 11, 2007 in U.S. Appl. No. 11/048,040.
Notice of Non-Compliant Amendment mailed Jun. 1, 2007 in U.S. Appl. No. 11/048,040.
Amendment and Response and RCE filed May 21, 2007 in U.S. Appl. No. 11/048,040.
Final Rejection mailed Nov. 20, 2006 in U.S. Appl. No. 11/048,040.
Amendment and Response filed Sep. 5, 2006 in U.S. Appl. No. 11/048,040.
Non-final Rejection mailed Jul. 18, 2006 in U.S. Appl. No. 11/048,040.
Final Rejection mailed Jul. 9, 2008 in U.S. Appl. No. 11/151,563.
Amendment and Response filed Apr. 18, 2008 in U.S. Appl. No. 11/151,563.
Non-final Rejection mailed Jan. 29, 2008 in U.S. Appl. No. 11/151,563.
Amendment and Response and RCE filed Nov. 13, 2007 in U.S. Appl. No. 11/151,563.
Advisory action mailed Oct. 1, 2007 in U.S. Appl. No. 11/151,563.
Amendment and Response filed Sep. 11, 2007 in U.S. Appl. No. 11/151,563.
Final Rejection mailed Jun. 11, 2007 in U.S. Appl. No. 11/151,563.
Amendment and Response filed Mar. 19, 2007 in U.S. Appl. No. 11/151,563.
Non-final rejection mailed Oct. 19, 2006 in U.S. Appl. No. 11/151,563.
http://www.ipc.bas.bg/book1.htm (webpage regarding Exerowa et al., Foam and Foam Films; Theory, Experiment, Application, published by Elsevier (Dec. 1997)).
Final rejection mailed Sep. 19, 2008 in U.S. Appl. No. 11/312,559.
Office Action mailed Jul. 8, 2009 in U.S. Appl. No. 11/507,626.
Office Action mailed Mar. 19, 2009 in U.S. Appl. No. 11/507,626.
Office Action mailed Oct. 3, 2008 in U.S. Appl. No. 11/507,626.
Office Action mailed Oct. 21, 2008 in U.S. Appl. No. 11/151,563.
Office Action mailed Jul. 14, 2009 in U.S. Appl. No. 11/312,559.
Office Action mailed Mar. 16, 2009 in U.S. Appl. No. 11/312,559.
Office Action mailed Feb. 13, 2009 in U.S. Appl. No. 11/312,559.
Office Action mailed Dec. 4, 2008 in U.S. Appl. No. 11/312,559.
Notice of Allowance mailed Jun. 2, 2009 in U.S. Appl. No. 11/151,563.
Complaint. *3M Company and 3M Innovative Properties Company* v. *Gojo Industries, Inc*. United States District Court for the District of Minnesota. Case No. 0:10cv04065. Filed Sep. 28, 2010.
Interview Summary dated Jul. 14, 2009 for U.S. Appl. No. 11/312,559, filed Dec. 21, 2005.
European Patent Specification EP 1 811 013 B1 published Aug. 12, 2009.
Request for Foreign Priority mailed Aug. 19, 2009 for U.S. Appl. No. 11/312,559, filed Dec. 21, 2005.
Request for RCE dated Sep. 1, 2009 in U.S. Appl. No. 11/151,563, filed Jun. 13, 2005.
Notice of Allowability dated Sep. 21, 2009 in U.S. Appl. No. 11/151,563, filed Jun. 13, 2005.
Non-Final Rejection mailed Sep. 17, 2009 for U.S. Appl. No. 12/032,083, filed Feb. 15, 2008.
Response dated Oct. 12, 2009 to European Patent Application No. 08250626.2.
Canadian Examination Report dated Oct. 13, 2009 in Application Serial No. 2,595,025.
Notice of Allowability mailed Oct. 13, 2009 in U.S. Appl. No. 11/312,559, filed Dec. 21, 2005.
Office Action dated Oct. 15, 2009 in U.S. Appl. No. 11/438,664, filed May 22, 2006.
Examination Report dated Jul. 20, 2009 for New Zealand Patent Application No. 561741.

U.S. Appl. No. 12/514,326, filed May 11, 2009 and entitled "Compositions, in Particular Cream to Protect Against Cold".
Notice of Allowance and Fee(s) Due and Notice of Allowability mailed Nov. 24, 2009 for U.S. Appl. No. 11/151,563, filed Jun. 13, 2005.
Interview Summary with Notification Date of Nov. 24, 2009 for U.S. Appl. No. 11/312,559, filed Dec. 21, 2005.
Office Action for Canadian Patent Application No. 2,540,085 dated Oct. 29, 2008.
Examiner's first report on Australian Patent Application No. 2004 275900 dated May 21, 2009.
Rosen, Milton J., Dahanayake, Manilal. *Industrial Utilization of Surfactants Principles and Practice*. 2000.
Product Information 3M Flourad™.
Response to Opposition (European Patent Application No. 06256249.1/European Patent No. EP 1 811 013) as filed by Ecolab, Inc. By Gojo Industries, Inc. dated Dec. 20, 2010.
U.S. Office Action mailed Jan. 19, 2011 for U.S. Appl. No. 11/075,287, filed Mar. 8, 2005.
U.S. Office Action mailed Jan. 19, 2011 for U.S. Appl. No. 11/369,381, filed Mar. 7, 2006.
Protest Under 37 C.F.R. 1.291 electronically filed on Dec. 20, 2010 for U.S. Appl. No. 12/878,786, filed Sep. 9, 2010.
U.S. Office Action mailed Dec. 13, 2010 for U.S. Appl. No. 12/878,786, filed Sep. 9, 2010.
Protest Under 37 C.F.R. 1.291 electronically filed on Dec. 20, 2010 for U.S. Appl. No. 12/878,793, filed Sep. 9, 2010.
U.S. Office Action mailed Dec. 10, 2010 for U.S. Appl. No. 12/878,793, filed Sep. 9, 2010.
U.S. Office Action mailed Dec. 13, 2010 for U.S. Appl. No. 12/552,126, filed Sep. 1, 2009.
Amendment electronically filed on Nov. 2, 2010 for U.S. Appl. No. 11/075,287, filed Mar. 8, 2005.
Response in European Patent Application No. 08250626.2 in the name of Gojo Industries, Inc. dated Dec. 12, 2009.
Supplemental Response and Amendment electronically filed on Aug. 13, 2010 for U.S. Appl. No. 12/032,083, filed Feb. 15, 2008.
U.S. Office Action mailed Aug. 3, 2010 for U.S. Appl. No. 11/075,287, filed Mar. 8, 2005.
U.S. Office Action mailed Aug. 3, 2010 for U.S. Appl. No. 11/369,381, filed Mar. 7, 2005.
Information Disclosure Statement electronically filed on Nov. 19, 2010 for U.S. Appl. No. 12/624,073, filed Nov. 23, 2009.
U.S. Office Action mailed Nov. 23, 2010 for U.S. Appl. No. 12/179,410, filed Jul. 24, 2008.
Gojo submission of Feb. 15, 2012 in the Opposition to European Patent No. 1 811 013 B1 (including Auxiliary Claim Sets).
Declaration of Evan Hillman and Annexes submitted in the Opposition to European Patent No. 1 811 013 B1.
Declaration of Amanda J. Copeland and Annexes submitted in the Opposition to European Patent No. 1 811 013 B1.
Submission by Deb Worldwide Healthcare, Inc. in the Opposition to European Patent No. 1 811 013 B1 (including Exhibit E).
Reply dated Dec. 30, 2011 to the European Patent Office Communication dated Jun. 20, 2011 by 3M regarding 06 77 2279.3, including an Amended set of claims (marked-up version and clean copy) and Acknowledgment of receipt.
Examiner's Answer mailed Feb. 9, 2012 to Appeal Brief filed Jul. 18, 2011 for U.S. Appl. No. 11/369.381.
Request for Oral Hearing filed Feb. 8, 2012 in U.S. Appl. No. 12/179,410.
Amendment and Response dated Feb. 12, 2007 in U.S. Appl. No. 11/340,778.
Amendment and Response dated Sep. 11, 2008 in U.S. Appl. No. 11/340,778.
Preliminary Amendment dated Aug. 22, 2006 for U.S. Appl. No. 11/507,626.
Translation of Communication from the European Patent Office in Veeger et al, EP 05 825 981.3 (counterpart to US Appl. No. 12/624,073).
Office Action dated Oct. 26, 2011 in U.S. Appl. No. 11/075,287, filed Mar. 8, 2005.

Appellant's Brief on Appeal dated Oct. 31, 2011 in U.S. Appl. No. 12/179,410, filed Jul. 24, 2008.
Office Communication from the US Patent Office dated Oct. 21, 2011 in U.S. Appl. No. 11/806,767, filed Jun. 4, 2007.
Office Communication from the US Patent Office dated Oct. 21, 2011 in U.S. Appl. No. 11/520,819, filed Sep. 14, 2006.
Translation of International Preliminary Report on Patentability from International Application No. PCT/EP2005/013742 dated Sep. 20, 2007.
Office Action from the Chinese Patent Office (translation) dated Aug. 25, 2010 for Application No. 200680015637.1.
Response to Canadian Patent Office dated May 26, 2010 for Application No. 2,540,085.
Amendments submitted to EPO dated May 26, 2010 for Application No. 06705273.8.
Response to the Australian Patent Office dated Mar. 23, 2010 for Application No. 2004275900.
Response to the Canadian Patent Office dated Mar. 18, 2010 for Application No. 2,595,025.
Amendment filed with the New Zealand Patent Office dated Dec. 21, 2009 for Application No. 561741.
Response to the Canadian Patent Office dated Dec. 22, 2009 for Application No. 2,540,085.
Response to the New Zealand Patent Office dated Nov. 19, 2009 for Application No. 561741.
Response to Canadian Patent Office dated Nov. 10, 2009 for Application No. 2,595,025.
Office Action from the Ukranian Patent Office (translation) dated Jul. 30, 2009 for Application No. a 200710192/M.
Office Action dated May 10, 2011 in U.S. Appl. No. 12/878,786.
Office Action dated May 10, 2011 in U.S. Appl. No. 12/878,793.
Office Action dated Apr. 29, 2011 in U.S. Appl. No. 12/552,126.
Office Action dated Mar. 25, 2011 in U.S. Appl. No. 12/624,073.
Communication dated Mar. 9, 2011 in the opposition to European Patent 1 811 013.
Amendment dated Feb. 23, 2011 in U.S. Appl. No. 12/179,410.
Amendment and Response dated Feb. 18, 2011 in U.S. Appl. No. 12/878,786.
Amendment and Response dated Feb. 18, 2011 in U.S. Appl. No. 12/878,793.
Amendment and Response dated Feb. 18, 2011 in U.S. Appl. No. 12/552,126.
Office Action dated May 24, 2011 in U.S. Appl. No. 12/179,410.
Office Action dated Feb. 15, 2011 in U.S. Appl. No. 11/806,767.
Request for Certificate of Correction for US Patent No. 7,651,990 (U.S. Appl. No. 11/151,563) mailed Jun. 20, 2011.
Communication dated Jun. 20, 2011 in European Application No. 06 772 279.3.
Communication dated Apr. 26, 2010 in European Application No. 04786634.8.
Response to Office Action and Amendments dated Oct. 7, 2010 for Canadian Application No. 2,595,025.
Communication dated Jan. 1, 2010 in European Application No. 04786634.8.
Office Action dated May 26, 2011 in U.S. Appl. No. 12/659,063.
Appellant's Brief on Appeal dated Jun. 13, 2011 in U.S. Appl. No. 11/075,287.
Appellant's Brief on Appeal dated Jun. 14, 2011 in U.S. Appl. No. 11/369,381.
Reply from Australian Patent Office dated Jun. 1, 2010 for Application No. 2005318384.
EP 1 233 749 issued Nov. 21, 2000, Biering, Holger (English-language claims).
Brochure, Polyox Water-Soluble Resins, Nordmann, Rassmann GmbH, Hamburg, Germany, Dec. 16, 2004 or earlier.
DE 10 2004 062 775 A1 filed on Dec. 21, 2004 (Certified translation).
The Dow Chemical Company Sales Specification for Specified Material 00029789-S: Ethocel Standard 100 Industrial Ethylcellulose printed Sep. 11, 2001.
The Dow Chemical Company Sales Specification for Specified Material 00116267-S: Ethocel Standard 300 Industrial Ethylcellulose printed Sep. 11, 2001.
The Dow Chemical Company Sales Specification for Specified Material 00129064-S: Polyox™ WSR N10 Amerchol printed Feb. 28, 2003.
The Dow Chemical Company Sales Specification for Specified Material 00129042-S: Polyox™ WSR N3000 Amerchol printed Feb. 18, 2003.
The Dow Chemical Company Sales Specification for Specified Material 00126141-S: Polyox™ WSR N60K printed Feb. 18, 2003.
Toxicological Test Results From Literature, Final Report of the Safety Assigment of Dimethicone Copolyol, Journal of American College of Toxicology, vol. 1, No. 4, 1982 dated Jul. 30, 2001 (Goldschmidt Personal Care—Degussa).
Floyd, et al., "Performance-Drive: New Silicone Copolymers," Global Cosmetics Industry, Sep. 2000.
Degussa Creating Essentials, Product Data Record for ABIL® B 8832 (3 pages) dated Jul. 14, 2004, Mat. No. 202534, Edition 1.
Degussa, Product Specification for ABIL® B 8832 (1 page) dated Aug. 26, 2004 (printed Sep. 6, 2004), Spec. No. ST-980121.
Degussa, Summary of toxicological and ecotoxicological data for ABIL® B 8832 (3 pages) dated May 17, 2002.
Dow PowerPoint Presentation entitled: "METHOCEL Applications in Personal Cleansing, a Superior Sensory Experience", Dec. 9, 2004 or earlier.
Dow PowerPoint Presentation entitled: ETHOCEL General Properties (15 pages, Dec. 9, 2004 or earlier).
Response to the Chinese Patent Office dated May 18, 2011 in Application No. 200680015637.1.
Office Action dated Apr. 11, 2011 in U.S. Appl. No. 11/806,767.
Office Action dated Apr. 13, 2011 in U.S. Appl. No. 11/520,819.
Office Action dated Mar. 28, 2012 in U.S. Appl. No. 13/095,698.
Amendment dated Jun. 28, 2012 in U.S. Appl. No. 13/095,698.
Deb Worldwide Healthcare Inc. and Deb Canadian Hygiene Inc., Plaintiffs, and Ecolab Co., Defendant, Court File No. T-379-11, Deb's Statement of Claim dated Mar. 7, 2011.
Deb Worldwide Healthcare Inc. and Deb Canadian Hygiene Inc., Plaintiffs, and Ecolab Co., Defendant, Court File No. T-379-11, Ecolab's Statement of Defense and Counterclaim dated Jun. 3, 2011.
Deb Worldwide Healthcare Inc. and Deb Canadian Hygiene Inc., Plaintiffs, and Ecolab Co., Defendant, Court File No. T-379-11, Deb's Reply and Defence to Counterclaim dated Jul. 11, 2011.
Deb Worldwide Healthcare Inc. and Deb Canadian Hygiene Inc., Plaintiffs, and Ecolab Co., Defendant, Court File No. T-379-11, Ecolab's Reply to Defence to Counter dated Jul. 11, 2011.
Deb Worldwide Healthcare Inc., Applicants and Kimberly-Clark Australia Pty. Ltd., No. VID 294 of 2011, Statement of Cross-Claim dated Aug. 2, 2011 (Federal Court of Australia, District Victoria, General Division).
Deb Worldwide Healthcare Inc., Applicants and Kimberly-Clark Australia Pty. Ltd., No. VID 294 of 2011, Notice of Filing, Statement of Claim and Certificate of Legal Representation dated Apr. 18, 2011 (Federal Court of Australia, District Victoria, General Division).
Amendment in U.S. Appl. No. 12/624,073, filed Jul. 29, 2011.
Amendment in U.S. Appl. No. 12/787,624, filed Jul. 19, 2011.
Notice of Allowance in U.S. Appl. No. 12/787,624 mailed on Aug. 5, 2011.
Communication in European Application No. 06 772 279.3—2108 dated Jun. 20, 2011.
Office Action dated May 13, 2011 in U.S. Appl. No. 12/787,624.
Acknowledgement of documents and Summons to Attend Oral Proceedings dated Sep. 9, 2011 for EP Patent No. 18110130.
Wang, et al., "Direct Force Measurement of Comb Silicone Surfactants in Alcoholic Media by Atomic Force Microscopy", Journal of Colloid and Interface Science 242, 337-345 (2001).
Prieto et al., "Structure-function relationships of dimethicone copolyol", j. Cosmet. Sci., 51, 91-101 (Mar./Apr. 2000).
Japanese Patent Application No. 2008-500017, Drafting Date: May 26, 2011, Mailing Date: May 31, 2011 "Notice of Reasons for Rejection".

Japanese Publication No. 06-327750 published Nov. 29, 1994, "English Abstract of Reference 2".

Notice of Reasons for Rejection for Canadian Patent Application No. 2008-500017 mailed Jan. 17, 2012.

Mason Chemical Company, brochure for Masurf FS-115/FS-130 100504.

Decision in the Opposition to European Patent No. 1 811 013 B1 (including Auxiliary Requests) dated Apr. 10, 2012.

Notice of Reasons for Rejection for Canadian Patent Application No. 2008-500017 mailed May 31, 2011.

US 7,754,762, 07/2010, Wegner et al. (withdrawn)

* cited by examiner

HIGH ALCOHOL CONTENT FOAMING COMPOSITIONS WITH SILICONE-BASED SURFACTANTS

CROSS REFERENCE TO RELATED U.S. APPLICATIONS

This patent application relates to, and is a National Phase application claiming the benefit of PCT/CA2006/000320 filed on Mar. 7, 2006; which further claims the priority benefit from, U.S. Provisional Patent Application Ser. No. 60/658,580 filed on Mar. 7, 2005, in English, entitled HIGH ALCOHOL CONTENT FOAMING COMPOSITIONS WITH SILICONE-BASED SURFACTANTS, and which is incorporated herein by reference in its entirety.

FIELD OF THE INVENTION

The present invention relates to compositions with high contents of lower alcohol ($C_{1-4}$) that could be dispensed as a foam both under low pressure from unpressurized containers and from pressurized containers achieved with an aerosol packaging system. The compositions to be dispensed as foams contain a silicone-based surfactant and when mixed with air provide a stable alcohol foam which can be used for personal cleaning or for disinfecting purposes.

BACKGROUND OF THE INVENTION

Ethanol and/or Isopropyl alcohol and/or n-propyl alcohol compositions with at least 60% percent v/v (approximately 52% by weight) are well known to be antibacterial, therefore widely accepted for disinfecting purposes. Nonetheless due to the inherent characteristics of alcohol, it is perceived that the higher the content the better the product and a solution with higher than 60% by volume alcohol content is more desirable.

Alcohol disinfectant solutions are generally thickened in order to eliminate the waste and facilitate spreading the composition throughout the desired area. It is also known that other than gelling agents one can use paraffin or waxes to achieve thickening of a solution with high alcohol concentration. Such a composition with lanolin added to reduce the melting point closer to body temperature is described in U.S. Pat. No. 2,054,989. One of the disadvantages of gels and the above-mentioned type of thick alcohol-containing compositions is that if they do not leave a tacky feeling on the hands after one use (although some do); the effect builds up after repetitive use during the day, making it necessary to eventually wash off the thickeners before continuing the usage of an alcohol antiseptic solution. The present invention if formulated for the above-mentioned type of product does not leave such a feel, and does not need to be washed off after repeated use.

Generally speaking a high alcohol content disinfectant solution disinfects but does not clean. In order to make them disinfect and clean, so much soap would need to be added to the solution that the skin would feel soapy and disagreeable resulting in a formulation that would have little commercial appeal. Nonetheless, a non-irritant skin disinfecting formulation with a high content of a lower alcohol for use as a skin-washing agent has been successfully achieved by combining emulsifiers, surfactants and skin emollients as described in U.S. Pat. No. 5,629,006.

Surfactants other than for cleaning purposes are also used for spreading an aqueous composition containing one or more active substances rapidly and evenly over a surface due to their wetting properties. The use of good wetting agents definitely improves the efficient use of active substances in different compositions as described in U.S. Pat. No. 5,928,993.

Although a high alcohol content disinfectant solution has good disinfectant characteristics, it has a sharp smell and is generally perceived to cause drying of the skin, characteristics which can also be diminished to a desirable level in the present invention.

A foam product with greater than 40% v/v alcohol, which is easy and safe to use, is desirable over conventional liquid, gel or ointment type composition products. The concentration of alcohol already poses a hazard in itself, and there are many applications in which the perceived risk may be diminished if it could be dispensed as a foam. A foam intended to be useful as a skin disinfecting agent must have a uniform consistency, spreadability, cleansing ability, and have a pleasant feel, i.e. have rapid breaking power when pressure is applied; all of which present a challenge for a high lower alcohol content composition.

The description of an aqueous foaming skin disinfecting composition using 15% w/w alcohol as a co-solvent, which requires no pressurized container or added propellant to produce the foam, is described in U.S. Pat. No. 3,962,150.

The foam-forming agents utilized heretofore, have been incapable of forming stable foams when the liquid phase has high alcohol content without using other ingredients. Furthermore, lower alcohols have been considered to be defoamers rather than foam-promoting chemicals. According to Klausner, in U.S. Pat. No. 3,131,153, if more than 64% alcohol is used non-homogeneous compositions are obtained. The compositions in the patent required propellant to foam and the foams produced were of limited stability.

Various examples of compositions with a high content of a lower alcohol that are dispensed as a foam have been described, although for the purpose of the present invention the concentrations of alcohol and the levels of other ingredients are not suitable. More importantly, the use of propellants and aerosol containers to generate the foam is not desirable. For example, the compositions described in U.S. Pat. No. 5,906,808 disclose a product that uses an emulsifying wax NF, and a combination of stearyl and cetyl alcohol, or other wax combinations, which improve the foaming performance of the composition, in combination with cetyl lactate, to produce a 0.8% chlorhexidine gluconate alcohol product.

U.S. Pat. No. 5,167,950 issued to Lins discloses a foam product which requires a propellant and where no surfactant is added as a cleaning agent. The composition disclosed in this patent is based upon using an emulsifier system (fatty alcohol ROH 16-22 carbons) in combination with the use of a thickening agent (carbomer, klucel, etc.) to produce an antimicrobial aerosol mousse having a high alcohol content. The mousse includes alcohol, water, a polymeric gelling agent and a surfactant system comprising a C16-C22 alcohol, aerosol propellant and a non-ionic polyethoxylated surfactant.

Despite the work done to date it has been shown that there is little specific knowledge on how foams react and are formed, and surprisingly formulations that might seem not foamable result in the best foam producing ones while other formulations which seemed to have been producing foam even while being prepared did not perform well at all in some non-aerosol foam dispensers. The behaviour of aqueous foams is not the same as that of an alcohol foam.

Silicone-based surfactants have been used in applications requiring lowering of the surface tension and increased wetting properties, especially in applications that require materials to be compatible with solvent systems other than water and non-reactive to other components in the compositions.

Silicone surfactants are desirable since they can achieve relatively low surface tension levels with relatively low concentrations in the compositions of interest Commercial examples of the exploitation of the advantage of the low surface tension levels achieved using Silicone based surfactants are crop protection products, printing inks, paints, floor coatings, etc. The characteristics mentioned above make silicone surfactants a candidate for the intention of this patent.

It would be very advantageous to have alcohol based disinfecting formulations containing silicone-based surfactants which may be dispensed as a foam under low pressure conditions and/and or through an aerosol packaging system. Further, it would be very advantageous and desirable to find a foaming agent that could be used in concentrations that would allow it to be used in products that can remain in the area on which they have been applied and do not need to be rinsed or wiped off due to small amounts of residue remaining after evaporation. Thus it would also be very advantageous to provide foams that do not leave an unpleasant sticky after-feel as most commercial alcohol gel products are known to, or which clog up the dispensing equipment used to dispense the foams. Silicone-based surfactants are more than desirable for the purpose aforementioned since they are currently used as desirable cosmetic ingredients in creams, lotions, and other cosmetics due to their soft after-feel and properties.

SUMMARY OF THE INVENTION

The present invention provides high alcohol content compositions, which contain a surfactant/cleaning agent as well as a disinfectant/cleaning/solvent/carrier that causes very little drying to the skin or the hands of the user and is able to be dispensed as a foam from both pressurized and non-pressurized systems dispensing systems.

The present invention provides high alcohol content compositions that are able to be dispensed as a foam which are readily spread over the desired surface for the particular application. The present compositions can be formulated as an antimicrobial alcohol foam. The foamable compositions when dispensed from a suitable dispenser are stable and do not require the use of propellants and pressurized containers although if used would also foam.

Accordingly, the present invention provides foamable alcohol composition, comprising;

a) a $C_{1-4}$ alcohol, or mixtures thereof, present in an amount greater than about 40% v/v of the total composition;

b) an effective physiologically acceptable silicone-based surface active agent, which includes a lipophilic chain containing a silicone backbone ($-(R_2Si-O)_n-$), for wetting and foaming present in an amount of at least 0.01% weight percent of the total composition; and c) water present in an amount to balance the total composition to 100% weight percent.

In this aspect of the invention the effective silicone-based surface active agent is present in an amount from about 0.001% to about 10.0% weight percent of the total composition which is physiologically acceptable so it can be used in personal care type products.

In a preferred embodiment of the invention the silicone-based surfactant may be a Bis-PEG-[10-20] dimethicone, a 3-(3-Hydroxypropyl)-heptamethyltrisiloxane, an ethoxylated silicone-based surfactant, a Bis-PEG/PPG 18/6 Dimethicone, a Polyether-modified polysiloxane or a Polysiloxane betaine, or mixtures thereof. The present invention also provides an alcohol disinfecting composition, comprising;

a) a) an alcohol $C_{1-4}$, or mixtures thereof, present in an amount between about 60% to about 80% v/v of the total composition;

b) an effective physiologically acceptable silicone-based surface active agent for wetting and foaming present in an amount from about 0.01% to about 10.0% weight percent of the total composition;

c) a foam stabilizing agent present in an amount from about 0.01 to about 12.0% weight percent;

d) any one of moisturizers, emollients and combinations thereof present in an amount from about 0.05 to about 5.0% weight percent; and e) water in an amount to balance the total composition to 100% weight percent.

The present invention also provides a composition concentrate, comprising;

a) an effective silicone-based surface active agent for wetting and foaming present in an amount of at least 0.01% weight percent of the total composition 0.01 to about 15.0%;

b) a foam stabilizing agent including at least from about 0.01 to about 10.0%;

c) one of moisturizers, emollients and combinations thereof present in a range from about 0.05% to about 5.0%; and d) water.

DETAILED DESCRIPTION OF THE INVENTION

Definitions

The term "emollient" as used herein refers broadly to materials which are capable of maintaining or improving the moisture level, compliance, or appearance of the skin when used repeatedly.

The term "emulsifier" as used herein refers to surfactants or other materials added in small quantities to a mixture of two miscible liquids for the purpose of aiding in the formation and stabilization of an emulsion.

The phrase "emulsifying ingredients" as used herein is synonymous with emulsifier defined above.

The term "emulsion" as used herein refers to a colloidal dispersion of one liquid in another.

The term "surfactant" as used herein is the widely employed contraction for "surface active agents" which is the descriptive generic term for materials that preferentially adsorb at interfaces as a result of the presence of both, lipophylic and lipophobic structural units, the adsorption generally resulting in the alteration of the surface or interfacial properties of the system.

The term "silicone-based surfactant" as used herein refers to a surface active agent in which the lipophylic chain contains a silicone chain, also described as any organosilicon oxide polymer in which the structural unit is usually comprising: $-R_2Si-O)_n-$ where R is a monovalent organic radical, and which enables the composition in which it is contained to clean, wet and foam.

The phrase "foam stabilizer" as used herein refers to an additive that increases the amount or persistence of foam produced by a surfactant system.

The term "disinfect" as used herein means to destroy or reduce harmful microorganisms.

The phrase "physiologically acceptable" as used herein means a material that does not usually produce irritation or toxicity when applied to the skin and is acceptable by users to apply to human skin "Foam" as used herein means a liquid and a gas mixed to form a mass of small bubbles that has a structure that lasts for a variable length of time.

A bubble is a cell of gas surrounded by a film of liquid.

The term "aerosol" as used herein means a package and delivery system, and the product delivered, in which a pressurized gas is used to force the product out for dispensing. The gas may or may not be dispensed with the product.

An "aerosol foam" is a foam dispensed out of an aerosol package and delivery system as defined above.

The phrase "low pressure" in the context of producing a foam as used herein means a pressure of around an atmosphere or less such as when dispensing the foam from an unpressurized conainer. Typically when foams are dispensed from aerosol containers the foam is considered to be being dispensed under high "pressure" conditions.

The present invention provides foamable alcohol compositions which include silicone-based surfactants with high contents of lower alcohol ($C_{1-4}$) able to be dispensed as a foam under low pressure conditions from unpressurized containers and through an aerosol packaging system. The present foamable compositions when mixed with air deliver a stable foam to provide an alcoholic liquid solution which can be used for personal cleaning or for disinfecting purposes and which breaks on pressure application such as when a user rubs their hands or when applied over a surface. All percentages provided herein are based on the total weight unless otherwise indicated.

The alcohol used in the present invention is a lower hydrocarbon chain alcohol such as a $C_{1-4}$ alcohol. The preferred alcohol is chosen from ethanol, 2-propanol, or n-propanol, most preferably ethanol, well accepted by Health Care personnel as an adequate disinfectant at the right percentages. It will be appreciated by those skilled in the art that if the alcohol used in the formulation is ethanol or a combination of ethanol with one or more of the other $C_{1-4}$ alcohols the ethanol preferably will be properly denatured to meet the local regulations of the targeted markets, but for the purposes of this patent it will be referred just as ethanol without it being specific as to whether it has been denatured. The compositions may use a single alcohol or as mentioned a blend of two or more alcohols may comprise the alcohol content of the composition A significant and very surprising achievement of the present invention is that compositions suitable for disinfecting have been made containing greater than 40% v/v alcohol and a silicone-based surfactant able to be dispensed as a cosmetically appealing foam from both, low pressure conditions and through an aerosol packaging system.

The use of a silicone-based surfactant is the key ingredient as the primary foaming agent in the compositions designed to foam. Silicone surfactants have various interesting properties such as leaving little residue, being able to function in harsh chemical and thermal environments; they have an unparalleled wetting power, characteristics that are in general better than those of traditional surfactants, they show better surface-active properties in organic solvents, and that have made them widely used for applications in coatings, oilfield, material finishes, cleaning, paints, pesticides application, etc.

Traditional surfactants have carbon chains as the hydrophobic portion of the molecule. The hydrophile that is added to the carbon chain will determine the solubility and the general class of surface active agents as anionic, cationic, non-ionic or amphoteric. The silicone-based surfactants suitable for the compositions disclosed herein may include, but are not limited to, phosphate esters, sulphates, carboxylates, Imidazole quats, Amino Quats, Alkyl Quats, Amino propionates, ethoxylates, glycerol esters, amine oxides, acetylenic alcohol derivatives, phosphates, carbohydrate derivatives, sulfonates, betaines, Isethionates, esters, polyamides, and hydrocarbon surfactants that have a silicone chain —$(R_2$—$Si$—$O)_n$— and are compatible with the other components being used for a particular formulation.

From the different silicone surfactants commercially available, samples from different manufacturers and different chemical surfactant groups were evaluated. Particularly, the Silicone Polyethers, also known as dimethicone copolyols showed the best performance. Amongst them, samples of multi-pendant and linear-difunctional showed activity but the later was found to give superior foam properties. This is interesting as well as unexpected since in most water based applications if one of the multi-pendant or linear-difunctional silicone surfactants produces foam in water based mixtures, the other does not perform as well. However this is in agreement with the observations that foaming alcohol compositions behave quite differently from foaming water-based compositions.

While trying different surfactants, mixtures of two or more were evaluated to find out whether there was any synergy identifiable to optimize usage and foam performance. While some synergies were identified, it was also found that particularly difunctional silicone surfactants Bis-PEG [10-20] Dimethicones were the best when used alone. The notation Bis-PEG-[10-20] means all the Bis-PEG compounds having from 10 to 20 repeating oxyethylene groups. This applies to all other constituents as well. Specifically Bis-PEG 12 dimethicone and/or Bis-PEG-20 dimethicone and/or Bis-PEG-17 dimethicone are preferred along with 3-(3-Hydroxypropyl)-heptamethyltrisiloxane, ethoxylated, acetate, a polyether-modified polysiloxane and a polysiloxane betaine, showed promising results but not as good as the dimethicone ones.

In preferred embodiments of the compositions, the effective silicone-based surface active agent may be a physiologically acceptable Bis-PEG-[10-20] dimethicone, a 3-(3-Hydroxypropyl)-heptamethyltrisiloxane, ethoxylated, acetate, a Polyether-modified polysiloxane or a Polysiloxane betaine, or mixtures thereof from about 0.01% to about 10.0% weight percent of the total composition.

It was surprisingly found that despite the characteristics of silicone-based surfactants, there is little or no information on their use to produce a foamable product with high alcohol content under either, low pressure conditions or through an aerosol packaging system.

Furthermore, in order to obtain a high alcohol content product able to produce a foam even if no pressurized containers or propellants are used, surface tension values as low as possible are required so that the pressure required to produce such foam by hand pumps and mechanical means would be sufficient.

During the development of the present invention, it was unexpectedly found that a relatively stable quick breaking foam could be obtained when using just ethanol and the silicone-based surfactant with as high as 80% v/w while using traditional surfactants at higher percentage yielded results that could not be even slightly similar and no foam at all could be obtained.

In order to achieve a commercially suitable formulation (one that lasts long enough for the purpose of use in disinfecting applications), reducing the amount of silicone-based surfactant used while using the assistance of other ingredients such as secondary surfactants, emulsifiers, foam stabilizers, fragrances, and the like ingredients employed in cosmetics, aerosols, toiletries, personal care, etc. is one of the approaches that were followed. One of the commercial products obtained uses emulsifiers and polyethoxylated fatty acid surfactants disclosed in U.S. Pat. Nos. 5,167,950 and 6,090,395, both incorporated herein by reference, while other examples use a combination of different foam stabilizers to achieve a similar result.

Examples of secondary surfactants that may be used in the present compositions include other silicone surfactants, fluorinated surfactants, alkylglucosides, a poly(ethoxylated and/or propoxylated)alcohol, a poly(ethoxylated and/or propoxylated)ester, a derivative of a poly(ethoxylated and/or propoxylated)alcohol, a derivative of a poly(ethoxylated and/or propoxylated)ester, an alkyl alcohol, an alkenyl alcohol, an ester of a polyhydric alcohol, an ether of a polyhydric alcohol, an ester of a polyalkoxylated derivative of a polyhydric alcohol, an ether of a polyalkoxylated derivative of a polyhydric alcohol, a sorbitan fatty acid ester, a polyalkoxylated derivative of a sorbitan fatty acid ester, a betaine, a sulfobetaines, imidazoline derivatives, aminoacid derivatives, lecithins, phosphatides, some amine oxides and sulfoxides and mixtures thereof, present in an amount between about 0.10% to about 5% weight percent.

A preferred betaine is cocamidopropyl betaine. A preferred alkylglucoside is cocoglucoside. A preferred fluorinated surfactant is DEA C[8-18] perfluoroalkylethyl phosphate; another preferred fluorinated surfactant is Ammonium C[6-16] perfluoroalkylethyl phosphate, Preferred polyethoxylated fatty alcohols are polyethoxylated stearyl alcohol (21 moles ethylene oxide) and polyethoxylated stearyl alcohol (2 moles ethylene oxide), and a combination of these two.

The compositions may include an antimicrobial agent. The following antimicrobials are offered as non-limiting examples of suitable antimicrobials for use in the present invention and may include chlorhexidine salt, iodine, a complexed form of iodine, parachlorometaxylenol, triclosan, hexachlorophene, a phenol, behenyl alcohol, a surfactant having a long chain hydrophobic group and a quaternary group, hydrogen peroxide, silver, a silver salt, silver oxide, other quaternary ammonium salts and mixtures thereof.

A preferred antimicrobial agent in the present compositions is chlorhexidine gluconate (CHG) present in an amount between about 0.10% to about 4.0% weight percent. Another preferred antimicrobial agent is didecyl dimethyl diamonium chloride in an amount between about 0.05% to 5% weight percent. Another preferred antimicrobial agent is Benzalkonium chloride in an amount between about 0.05% to 5% weight percent. Another preferred anitimicrobial is Behenyl alcohol between 0.05-15% weight percent.

If the amount of ingredients employed is little enough not to leave a tacky feeling after the composition evaporates after single or multiple uses, and this is achieved while maintaining at least 60% v/v ethanol or n-propanol concentration or 70% v/v isopropanol, then the composition would be ideal for use as an alcohol hand sanitizer/disinfectant foamable composition.

The addition of water to the alcohol produces a more stable foam while allowing to reduce the amount of silicone-based surfactant required to foam the product. For example, using 0.5 to 1.0% silicone-based surfactant with a 50 to 60% v/v alcohol water solution produces a stable foam that does not readily collapse and that produces a stable puff that does not fall even when inverted and does not collapse until pressure is applied (such as when rubbed in hands or on over a surface) to provide an alcoholic liquid solution, while levels of up to 5% are required if the percentage of alcohol used is greater than 65% w/w.

The use of a mild non-irritant surfactant widely used in the cosmetic industry such as cocamidopropyl betaine or a fluorinated surfactant such as DEA C[8-18] perfluoroalkylethyl phosphate or Ammonium C[6-16] perfluoroalkylethyl phosphate as a secondary surfactant is more suitable to prepare the foamable hydroalcoholic composition of the present invention depending on the silicone-based surfactant being used.

In order to stabilize the foam, foam stabilizers, as well as emulsifying ingredients have been tried with good results in allowing the product to be dispensed as a foam even when no propellant and/or pressurized container systems are used.

Examples of compatible foam stabilizers that can optionally be employed include lactic acid esters of monoglycerides, cationic emulsifiers, triquaternized stearic phospholipid complex, hydroxystearamide propyltriamine salts, lactic acid monoglycerides, food emulsifiers such as glyceryl monostearate, Behentrimonium chloride, Cetrimonium chloride, propylene glycol monostearate, glycols, sodium stearoyl lactylate, silicone wax, an encapsulated oil, Microcapsule Mineral Oil.

A preferred foam stabilizer used in the present foamable compositions is cetyl betaine. Another preferred foam stabilizer is glycerine. Another preferred foam stabilizer is Cetrimonium chloride and also Behentrimonium chloride.

Examples of moisturizers and/or emollients which may be used in the present formulations include lanolin, vinyl alcohol, polyvinyl pyrrolidone and polyols selected from the group consisting of glycerol, propylene glycol, glyceryl oleate and sorbitol, cocoglucoside or a fatty alcohol selected from the group consisting of cetyl alcohol, stearyl alcohol, lauryl alcohol, myristyl alcohol and palmityl alcohol, cetyl alcohol, ceteareth 20, and combinations thereof, present in an amount up to about 5%. The compositions may include a lipid layer enhancer such as a mixture of alkylglucoside and glyceryl Oleate, or PEG-200 Hydrogenated Glyceryl Palmiate, or Dihydroxypropyl PEG-5 Linoleammonium Chloride or PEG-7 Glyceryl Cocoate.

The compositions are formulated to be dispensed as a foam from an unpressurized dispenser having a dispenser pump for mixing the composition with air and dispensing foam therefrom. Alternatively the composition may be packaged in an aerosol container and dispensed under high pressure conditions.

The present invention is unique in that it can be dispensed as a foam from such manual low pressure dispensing systems as described, however, the composition can alternatively be dispensed under high pressure systems as well.

The composition may include an aerosol propellant in an amount from about 3 to about 20 weight percent of the total composition for pressurized discharge of the foam. The aerosol propellant may include propane, carbon dioxide, butane, dichloro difluoro methane, dichloro tetra fluoro ethane, octafluorocyclo butane; 1,1,1,2-tetrafluoroethane; 1,1,1,2,3, 3,3 heptafluoropropane, and 1,1,1,3,3,3,-hexafluoropropane. When stored in a metal container with propellant, the formulation may include a corrosion inhibitor such as sorbic acid, benzoic acid, potassium sorbate and sodium benzoate, in an amount from about 0.1 to about 5 weight percent of the total composition.

The inventors have very surprisingly discovered that it is possible to produce alcohol foams which include a combination of both the silicone surfactants disclosed herein and fluorosurfactants disclosed in copending U.S. patent application Ser. No. 10/952,474, filed: Sep. 29, 2004 and PCT Publication WO 2005/030917 A1 with the resulting foam exhibiting an interesting synergy with respect to the foam quality.

While both types of surfactants in the extremes of the concentrations of alcohol covered produce more and better foam when the alcohol concentration is closer to 40% and produce a lower quality foam that does not last in concentrations higher than 80% it was very interestingly found that the foam quality observed with fluorosurfactants is different from that obtained using silicone based surfactants.

With the pumps used for the examples, compositions using fluorinated surfactants are as described as an aereated "quick" breaking foam disappearing within seconds depending on the amount of alcohol and percentage of surfactant used, while with the silicone based surfactants the foam has a distinctive different appearance, it appears to be more dense and sometimes looks more uniform giving the appearance to be "whiter" not necessarily because there might seem to be more bubbles but because the bubbles last longer, they are more stable.

The difference is better observed when comparing side-by-side samples containing the same percentage of alcohol, and while it is evident that when the foam is first dispensed it shows more volume and a "better" quality appearance if a fluorinated surfactant is used, this visual advantage is observed only during the first few seconds since the foam quite rapidly breaks down to a smaller volume to more resemble the foam obtained with the silicone-based surfactant. The most important difference appears to be how long the foam containing only the silicone-based surfactant lasts compared to the time the foam lasts with a foam containing only the fluorinated surfactant.

It should also be noted that one of the main differences in using one surfactant or the other (fluorosurfactants versus silicone surfactants) is the fact that fluorinated surfactants can reduce the surface tension to lower levels than those achieved using silicone-based surfactants alone, therefore compositions with only silicone based surfactants generally need a higher percentage of the silicone based surfactants to achieve a similar result.

A significant advantage to mixing both types of surfactants in the same composition is that the silicone based surfactant gives a longer lasting effect while the fluorinated surfactant has a better tolerance at higher levels of alcohol hence when mixed the combination provides an improvement in foam quality greater than obtaining using either one individually under some conditions.

Combining the surfactants allows the achievement of the desired foaming effect without exceeding solubility limits of either surfactant while at the same time taking advantage of the particular characteristics of the foam differences produced by each one.

The combination of silicone-based surfactants and fluorinated surfactant is of increasing advantage as the alcohol concentration increases, which is desirable to improve the microbiological efficacy.

The following non-limiting examples are set forth to show for the various preferred embodiments and are not in any way to limit the scope of the present invention.

EXAMPLES

Examples 1 through 12 were prepared to illustrate the ability to produce alcohol-based disinfecting formulations which can be dispensed as foams using different surfactants and a solution of water and 50% ethanol. Examples 13 through 16 illustrate increasing concentrations of a silicone-based surfactant to produce foam with 40% ethanol. Examples 17 through 32 show increasing concentrations of ethanol with different silicone-based surfactants to produce foam. Examples 33 through 36 illustrate increasing concentrations of a silicone-based surfactant to produce acceptable foam at 62% ethanol. Examples 37 through 52 illustrate the ability to produce foam using different surfactants and a solution of 70% v/v Isopropanol. All parts and percentages are expressed by weight unless otherwise indicated.

Comparatively, it was also found that for instance, Cocamidopropyl betaine (CAPB) alone even at 40% ethanol and at 3% CAPB, was unable to produce as good results as those with 60% v/v ethanol, and Silicone-based surfactants using much less percentage (less than 1.0%). Cocamidopropyl betaine does not give any acceptable foam above that percentage of alcohol and the lower than 60% v/v alcohol content makes it inadequate for a sanitizing solution. Also the solution left an unacceptable feeling on the skin after the alcohol evaporated (i.e. a soapy sticky feeling) indicating high levels of surfactant. Advantageously, the afterfeel of the present compositions was not only not soapy but actually pleasant makes the present invention suitable for many different applications.

The following examples were intended to evaluate the foaming ability of different groups of Silicon surfactants with different combinations of ethanol, n-propyl alcohol and Isopropyl alcohol. They were also designed to asses the effect in the after feel as well as in the foam quality of some emollients and humectants, lipids, and other cosmetic type desired ingredients to be used with a leave-on hand sanitizer product. Some ingredients with antibacterial properties were also added to again evaluate their effect on foam quality and after feel.

Examples 53 to 293 have total alcohol contents from 61% w/w to 75% w/w. The best foam was achieved with only ethanol as the alcohol, with the next best being the combination Ethanol and n-propyl alcohol using up to 10% n-propyl alcohol. The worst foams were those obtained using only Isopropyl alcohol and/or n-propyl alcohol. Also interesting is the fact that the surfactant that works the best with just ethanol is not the same that works the best with the other 2 alcohols tried. More specifically it was found that the PEG-17-Dimethicone as well as the Bis-PEG/PPG 18/6 Dimethicone work better than the Bis-PEG 12—Dimethicone with just n-propyl alcohol and/or Isopropyl alcohol. While combining different silicone surfactants if different alcohols are used seems to show a synergy to boost the foam when the addition of another alcohol disrupts the foaming ability of a particular silicone surfactant in the end the preferred silicone for the combination of alcohols emollients and other ingredients lies amongst the Bis-PEG [10-20] Dimethicone silicone surfactants.

Combinations of silicone surfactants with other surfactants were also tried; various experiments showed that although it was possible to find acceptable foam quality improvement when using other surfactants, the soapy after-feel was unacceptable for a leave-on product for many surfactants. However the compositions combining silicone surfactants with fluorosufactants mentioned above showed an improvement that very advantageously allows for the reduction in the percentage of silicone surfactant to optimize percentages in the formulation regarding cost and other efficacy desired outcomes.

While some cosmetic ingredients like Cocoglucoside Glyceryl Oleate appear to deteriorate the foam quality when present in the composition, if the after-feel effect is beneficial increasing then the foam quality may be improved by increasing the percentage of surfactant present and/or adding a foam stabilizer to the composition to improve the foam quality.

It was also interesting to find that while a higher percentage of silicone surfactant present in the composition has been observed to increase the quality of the foam, the increased amount of silicone surfactant present has to be considerable before an improvement is observed. For example, the foam quality achieved with 1% was not significantly better with 1.5% but was considerably better with 2% and the foam quality using 3% or 4% was very similar while 5% was much better than just 3%.

The quality of the dispensed foam can be dependant upon the characteristics of the pump mechanism used for dispensing the foam from a bottle. For instance the quality of the foam was better with the smaller shot size of 0.75 ml than the bigger shot size of 1.5 ml from a pump for the same size bottle. The shot size is the amount of liquid dispensed when the pump is activated.

From the above examples it can be concluded that they are clearly denoting how the art of foaming alcohol is different form that of foaming water based composition in more than one aspect and that unexpected outcomes could arise depending on the combination of ingredients desired for the final formulation in combination with the type of foaming device/mechanism to use.

Below are some more specific examples for compositions following a formulation to produce alcohol/silicone-surfactant hand/skin sanitizing foamable compositions; more than one being a foamable disinfecting composition with only alcohol being the only disinfectant ingredient, while other foamable disinfecting compositions use an added antimicrobial such as Chlorhexidine Digluconate or Didecyl Dimethyl Diammonium Chloride, Benzalkonium Chloride, Behenyl alcohol, etc.

Example 294

Alcohol Hand Sanitizing Foamable Disinfecting Composition 0.01-5.0%* silicone-based surfactant (primary surfactant)
0.01-1.0% cocoamidopropylbetaine (secondary surfactant)
0.05-1.0% cetyl betaine (foam stabilizing agent)
0.10-1.5% emulsifier fatty alcohol ROH 16-22 carbons or combination that works well in a final formulation containing
60-70% v/v ethanol
Q.S. water
  Preferably a Bis-PEG-[10-20] dimethicone, a 3-(3-Hydroxypropyl)-heptamethyltrisiloxane, ethoxylated, acetate, a Bis-PEG/PPG 18/6 Dimethicone, acetate, a Polyether-modified polysiloxane or a Polysiloxane betaine, or mixtures thereof.

Example 295

Alcohol Hand Sanitizing Foamable Disinfecting Composition Concentrate 0.1-5.0%* a physiologically acceptable silicone-based surfactant*; (primary surfactant)
0.001-12.0% 1,3 Butyleneglycol, 2-Butoxyethanol, or glycerin (foam stabilizing agents)
0.05-5.0% cocoglucoside, glyceryl oleate (moisturizers, emollients and the like)
60-70% v/v ethanol, n-propanol, isopropanol or a combination thereof
Q.S. water
  Preferably a Bis-PEG-[10-20] dimethicone, 3-(3-Hydroxypropyl)-heptamethyltrisiloxane, ethoxylated, acetate, a Bis-PEG/PPG 18/6 Dimethicone, acetate, a Polyether-modified polysiloxane or a Polysiloxane betaine, or mixtures thereof.

Example 296

Alcohol Hand Sanitizing Foamable Disinfecting Composition 0.01-5.0%* silicone-based surfactant (primary surfactant)
0.01-1.0% fluorinated surfactant and or other silicone-based surfactants or mixtures (secondary surfactant/s)
0.05-1.0% Cetrimonium Chloride (foam stabilizing agent)
0.05-1.0% Behentrimonium Chloride (foam stabilizing agent)
0.10-1.5% Dihydroxypropyl PEG-5 Linoleammonium Chloride, Glyceryl Oleate, PEG-200 Hydrogenated Glyceryl Palmate, Behenyl PG-Trimomium chloride, PEG-7 Glyceryl Cocoate or combination of emollients, lipids, humectants that works well in a final formulation containing
1-10% n-propyl alcohol
60-70% v/v ethanol
Q.S. water
  Preferably a Bis-PEG-[10-20] dimethicone, a 3-(3-Hydroxypropyl)-heptamethyltrisiloxane, an ethoxylated, a Bis-PEG/PPG 18/6 Dimethicone, acetate, a Polyether-modified polysiloxane or a Polysiloxane betaine, or mixtures thereof.

Example 297

Alcohol Hand Sanitizing Foamable Disinfecting Composition 0.01-5.0%* silicone-based surfactant (primary surfactant)
0.05-1.0% Cetrimonium Chloride (foam stabilizing agent)
0.05-1.0% Behentrimonium Chloride (foam stabilizing agent)
0.10-1.5% Dihydroxypropyl PEG-5 Linoleammonium Chloride, Glyceryl Oleate, PEG-200 Hydrogenated Glyceryl Palmate, Behenyl PG-Trimomium chloride, PEG-7 Glyceryl Cocoate or combination of emollients, lipids, humectants that works well in a final formulation containing
1-10% n-propyl alcohol
60-70% v/v ethanol
Q.S. water
  Preferably a Bis-PEG-[10-20] dimethicone, a 3-(3-Hydroxypropyl)-heptamethyltrisiloxane, an ethoxylated, a Bis-PEG/PPG 18/6 Dimethicone, acetate, a Polyether-modified polysiloxane or a Polysiloxane betaine, or mixtures thereof.

Example 298

Alcohol Hand Sanitizing Foamable Disinfecting Composition 0.01-5.0%* silicone-based surfactant (primary surfactant)
0.01-1.0% fluorinated surfactant and or other silicone-based surfactants or mixtures (secondary surfactant/s)
0.05-1.0% Cetrimonium Chloride (foam stabilizing agent)
0.05-1.0% Behentrimonium Chloride (foam stabilizing agent)
0.10-1.5% Dihydroxypropyl PEG-5 Linoleammonium Chloride, Glyceryl Oleate, PEG-200 Hydrogenated Glyceryl Palmate, Behenyl PG-Trimomium chloride, PEG-7 Glyceryl Cocoate or combination of emollients, lipids, humectants that works well in a final formulation containing
60-70% v/v ethanol
Q.S. water
  Preferably a Bis-PEG-[10-20] dimethicone, a 3-(3-Hydroxypropyl)-heptamethyltrisiloxane, an ethoxylated, a Bis-PEG/PPG 18/6 Dimethicone, acetate, a Polyether-modified polysiloxane or a Polysiloxane betaine, or mixtures thereof.

Example 299

Alcohol Hand Sanitizing Foamable Disinfecting Composition 0.01-5.0%* silicone-based surfactant (primary surfactant)
0.05-1.0% Cetrimonium Chloride (foam stabilizing agent)
0.05-1.0% Behentrimonium Chloride (foam stabilizing agent)
0.10-1.5% Dihydroxypropyl PEG-5 Linoleammonium Chloride, Glyceryl Oleate, PEG-200 Hydrogenated Glyceryl Palmate, Behenyl PG-Trimomium chloride, PEG-7 Glyceryl Cocoate or combination of emollients, lipids, humectants that works well in a final formulation containing
60-70% v/v ethanol
Q.S. water
   Preferably a Bis-PEG-[10-20] dimethicone, a 3-(3-Hydroxypropyl)-heptamethyltrisiloxane, an ethoxylated, a Bis-PEG/PPG 18/6 Dimethicone, acetate, a Polyether-modified polysiloxane or a Polysiloxane betaine, or mixtures thereof.

Example 300

Chlorhexidine Gluconate (CHG) & Alcohol Hand Sanitizing Foamable Disinfecting Composition Formulation 294, 295, 296, 297, 298 or 299 added with 0.50-4.0% Chlorhexidine Gluconate (CHG)

Example 301

Didecyl Dimethyl Diammonium Chloride & Alcohol Hand Sanitizing Foamable Disinfecting Composition Formulation 294, 295, 296, 297, 298 or 299 added with 0.01-5.0% Didecyl Dimethyl Diammonium Chloride

Example 302

Benzalkonium Chloride & Alcohol Hand Sanitizing Foamable Disinfecting Composition Formulation 294, 295, 296, 297, 298 or 299 added with 0.01-5.0% Benzalkonium Chloride

Example 300

Behenyl Alcohol & Alcohol Hand Sanitizing Foamable Disinfecting Composition

Formulation 294, 295, 296, 297, 298 or 299 added with 0.01-5.0% Behenyl Alcohol

The process to prepare the compositions of the present invention described
herein is straightforward since most of the ingredients are liquid. When wax type ingredients are to be used, they can be incorporated by warming up to 40-45° C. preferably to the water portion while mixing and then allowing it to cool down or they could be added in "cold", at room temperature to the alcohol before any other ingredient and mixed until completely incorporated before adding the rest of the ingredients according to the composition.

Active ingredients may be pre-dissolved into the water first, a process that will be well known to anyone skilled in the art. If a specific formulation cannot be adjusted to give the desired quality of foam with the preferred percentages of the different constituents, the characteristics of the dispensing mechanism may be modified to improve foam quality, for example the type and characteristics of the foaming pump, such as changing the air/liquid ratio, screen sizes at the nozzle, to mention a few, can be adjusted in ways which will be apparent to those skilled in the art.

The compositions described herein provide improved alcohol based disinfecting products over commercially available compositions with high concentrations of alcohol, as well as the fact they are able to foam without the use of propellants or pressurized containers, although it will be appreciated that using propellants may in some cases improve the quality of the resulting foam.

Depending on the alcohol concentration and the application of the particular composition the foam produced can widely vary, being at the high end of a relatively fast breaking foam variety which is stable enough to be thoroughly spread onto the skin without undue waste or effort.

The present formulations may be first made as a concentrate with only some of the constituents which can be shipped and then constituted with the remaining constituents. For example, the concentrate can include a) the effective silicone-based surface active agent for wetting and foaming present in an amount of at least 0.01% weight percent of the total composition 0.01 to about 15.0%, a foam stabilizing agent including at least from about 0.01 to about 10.0%, and any one of moisturizers, emollients and combinations thereof present in a range from about 0.05% to about 5.0%; and water.

The composition concentrate can then be constituted as an alcohol disinfecting composition by adding a) an alcohol $C_{1-4}$, or mixtures thereof, present in an amount between about 60% v/v to about 80% v/v of the total composition; and b) water present in an amount to balance the total composition to 100% weight percent.

Due to the nature of the base composition with respect to the alcohol concentration and the quality of the ingredients, an advantageous application for the present invention is as an alcohol skin/hand disinfectant composition for a foamable product, examples of which are described above.

Nevertheless, the present invention lends itself to the preparation of a wide variety of products for disinfecting applications, and it is to be understood that other embodiments may be utilized and that changes may be made without departing from the scope of the invention.

Consequently, it is intended that the claims be interpreted to cover such modifications and equivalents. To note a few, the following products may be produced using the alcohol/silicone-surfactants: medicated foams, sunscreen foams, hand cream foams, brush-less shaving cream foams, shower or bath oil foams, dry hair shampoo foams, make-up remover foams, analgesic foam rubs, hair grooming foams and antiperspirants hair cleaning foam, antiperspirant foam, hair conditioner foams.

As used herein, the terms "comprises", "comprising", "includes" and "including" are to be construed as being inclusive and open ended, and not exclusive. Specifically, when used in this specification including claims, the terms "comprises", "comprising", "includes" and "including" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

REFERENCES CITED

U.S. Patent Documents

| | | | |
|---|---|---|---|
| 2,054,989 | September 1936 | Moore | 167/58 |
| 3,131,153 | April 1964 | Klausner | 252/305 |
| 3,962,150 | June 1976 | Leonard et al. | 252/542 |
| 4,440,653 | April 1984 | James et al. | 252/8.55 |
| 5,167,950 | December 1992 | Lins | 424/47 |
| 4,956,170 | September 1990 | Lee | 514/772.1 |
| 5,629,006 | May 1997 | Minh et al. | 424/405 |
| 5,906,808 | May 1999 | Osborne, et al | 424/43 |
| 5,928,993 | July 1999 | Ingegärd | 504/116 |
| 5,951,993 | September 1999 | Scholz et al | 424/405 |
| 6,090,395 | July 2000 | Asmus et al | 424/401 |
| 6,610,315 | August 2003 | Scholz et al | 424/415 |
| 6,623,744 | September 2003 | Asmus et al | 424/401 |
| 6,562,360 | May 2003 | Scholz et al | 424/405 |

Other Publications

Myers, Drew; "Surfactant Science and Technology", second edition, Drew Myers, VCH Publishers, New York, 1992

| | Amount | | | | | |
|---|---|---|---|---|---|---|
| Ingredients | Ex. 1 | Ex. 2 | Ex. 3 | Ex. 4 | Ex. 5 | Ex. 6 |
| Ethanol | 50.00 | 50.00 | 50.00 | 50.00 | 50.00 | 50.00 |
| Silicone-based surfactant | 0.50 | — | — | — | — | — |
| Cocamidopropyl betaine (1) | — | 8.00 | — | — | — | — |
| Alkylglucoside (2) | — | — | 8.00 | — | — | — |
| Alkylglucoside (3) | — | — | — | 8.00 | — | — |
| Glycomul L | — | — | — | — | 8.00 | — |
| Sorbitan Sesquioleate | — | — | — | — | — | 8.00 |
| Purified Water | 49.50 | 42.00 | 42.00 | 42.00 | 42.00 | 42.00 |
| Total % | 100.00 | 100.00 | 100.00 | 100.00 | 100.00 | 100.00 |

(1) Amphoteric, (2) Nonionic, (3) Anionic

Examples 7-12

| | Amount | | | | | |
|---|---|---|---|---|---|---|
| Ingredients | Ex. 7 | Ex. 8 | Ex. 9 | Ex. 10 | Ex. 11 | Ex. 12 |
| Ethanol | 50.00 | 50.00 | 50.00 | 50.00 | 50.00 | 50.00 |
| Polysorbate 20 | 8.00 | — | — | — | — | — |
| Polyoxyethylene Sorbitan Monooleate | — | 8.00 | — | — | — | — |
| Sorbitan Monooleate | — | — | 8.00 | — | — | — |
| Cocamidopropyl betaine & sodium caproyl lactate | — | — | — | 8.00 | — | — |
| Cocamidopropyl hydroxysultaine | — | — | — | — | 8.00 | — |
| Sodium Cocoamphoacetate | — | — | — | — | — | 8.00 |
| Purified Water | 42.00 | 42.00 | 42.00 | 42.00 | 42.00 | 42.00 |
| Total % | 100.00 | 100.00 | 100.00 | 100.00 | 100.00 | 100.00 |

Examples 13-16

| | Amount | | | |
|---|---|---|---|---|
| Ingredients | Ex. 13 | Ex. 14 | Ex. 15 | Ex. 16 |
| Ethanol | 40.00 | 40.00 | 40.00 | 40.00 |
| Bis-PEG-20 dimethicone | 0.01 | — | — | — |
| 3-(3-Hydroxypropyl)-heptamethyltrisiloxane, ethoxylated, acetate | — | 0.01 | — | — |
| Polyether-modified polysiloxane | — | — | 0.01 | — |
| Polysiloxane betaine | — | — | — | 0.01 |
| Purified Water | 59.99 | 59.99 | 59.99 | 59.99 |
| Total % | 100.00 | 100.00 | 100.00 | 100.00 |

Examples 17-20

| | Amount | | | |
|---|---|---|---|---|
| Ingredients | Ex. 17 | Ex. 18 | Ex. 19 | Ex. 20 |
| Ethanol | 40.00 | 50.00 | 60.00 | 75.00 |
| Bis-PEG-20 dimethicone | 0.01 | 0.01 | 0.01 | 8.00 |
| Purified Water | 59.99 | 49.99 | 39.99 | 17.00 |
| Total % | 100.00 | 100.00 | 100.00 | 100.00 |

Examples 21-24

| Ingredients | Amount | | | |
|---|---|---|---|---|
| | Ex. 21 | Ex. 22 | Ex. 23 | Ex. 24 |
| Ethanol | 40.00 | 50.00 | 60.00 | 75.00 |
| Polysiloxane betaine | 1.0 | 1.0 | 1.0 | 8.00 |
| Purified Water | 59.00 | 49.00 | 49.00 | 17.00 |
| Total % | 100.00 | 100.00 | 100.00 | 100.00 |

Examples 25-28

| Ingredients | Amount | | | |
|---|---|---|---|---|
| | Ex. 25 | Ex. 26 | Ex. 27 | Ex. 28 |
| Ethanol | 40.00 | 50.00 | 60.00 | 75.00 |
| Polyether-modified polysiloxane | 1.0 | 1.0 | 1.0 | 1.0 |
| Purified Water | 59.00 | 49.00 | 39.00 | 24.00 |
| Total % | 100.00 | 100.00 | 100.00 | 100.00 |

Examples 29-32

| Ingredients | Amount | | | |
|---|---|---|---|---|
| | Ex. 29 | Ex. 30 | Ex. 31 | Ex. 32 |
| Ethanol | 40.00 | 50.00 | 60.00 | 75.00 |
| 3-(3-Hydroxypropyl)-heptamethyltrisiloxane, ethoxylated, acetate | 0.5 | 0.5 | 0.5 | 10.00 |
| Purified Water | 59.5 | 49.50 | 39.50 | 15.00 |
| Total % | 100.00 | 100.00 | 100.00 | 100.00 |

Examples 33-36

| Ingredients | Amount | | | |
|---|---|---|---|---|
| | Ex. 33 | Ex. 34 | Ex. 35 | Ex. 36 |
| Ethanol | 62.00 | 62.00 | 62.00 | 62.00 |
| Bis-PEG-20 dimethicone | 0.50 | 1.00 | 2.0 | 5.00 |
| Purified Water | 37.50 | 37.00 | 36.00 | 33.00 |
| Total % | 100.00 | 100.00 | 100.00 | 100.00 |

Examples 37-42

| Ingredients | Amount | | | | | |
|---|---|---|---|---|---|---|
| | Ex. 37 | Ex. 38 | Ex. 39 | Ex. 40 | Ex. 41 | Ex. 42 |
| 70% v/v Isopropanol | 99.90 | 92.00 | 92.00 | 92.00 | 92.00 | 92.00 |
| Silicone-based surfactant | 0.10 | — | — | — | — | — |
| Cocamidopropyl betaine (1) | — | 8.00 | — | — | — | — |
| Alkylglucoside (2) | — | — | 8.00 | — | — | — |
| Alkylglucoside (3) | — | — | — | 8.00 | — | — |
| Glycomul L | — | — | — | — | 8.00 | — |
| Sorbitan Sesquioleate | — | — | — | — | — | 8.00 |
| Total % | 100.00 | 100.00 | 100.00 | 100.00 | 100.00 | 100.00 |

(1) Amphoteric, (2) Nonionic, (3) Anionic

Examples 43-48

| Ingredients | Amount | | | | | |
|---|---|---|---|---|---|---|
| | Ex. 43 | Ex. 44 | Ex. 45 | Ex. 46 | Ex. 47 | Ex. 48 |
| 70% v/v Isopropanol | 92.00 | 92.00 | 92.00 | 92.00 | 92.00 | 92.00 |
| Polysorbate 20 | 8.00 | — | — | — | — | — |
| Polyoxyethylene Sorbitan Monooleate | — | 8.00 | — | — | — | — |
| Sorbitan Monooleate | — | — | 8.00 | — | — | — |
| Cocamidopropylbetaine & sodium caproyl lactate | — | — | — | 8.00 | — | — |
| Cocamidopropyl hydroxysultaine | — | — | — | — | 8.00 | — |
| Sodium Cocoamphoacetate | — | — | — | — | — | 8.00 |
| Total % | 100.00 | 100.00 | 100.00 | 100.00 | 100.00 | 100.00 |

Examples 49-52

| Ingredients | Ex. 49 | Ex. 50 | Ex. 51 | Ex. 52 |
|---|---|---|---|---|
| 70% v/v Isopropanol | 99.00 | 99.00 | 99.00 | 99.00 |
| Bis-PEG-20 dimethicone | 1.0 | — | — | — |
| 3-(3-Hydroxypropyl)-heptamethyltrisiloxane, ethoxylated, acetate | — | 1.0 | — | — |
| Polyether-modified polysiloxane | — | — | 1.0 | — |
| Polysiloxane betaine | — | — | — | 1.0 |
| Total % | 100.00 | 100.00 | 100.00 | 100.00 |

The solutions prepared, were evaluated as to whether foam was produced or not and if so, then the foam produced was described as follows:

| Example | Foam Produced | Foam Evaluation/Description/Characteristics |
|---|---|---|
| Ex. 1 | Yes | Very good stable stiff puff creamy and soft lasts a long time |
| Ex. 2 | No | Just Very Wet Bubbles produced lasting <10 seconds |
| Ex. 3 | No | — |
| Ex. 4 | No | — |
| Ex. 5 | No | — |
| Ex. 6 | No | Just Very Wet Bubbles produced lasting <7 seconds |
| Ex. 7 | No | Just Very Wet Bubbles produced lasting <10 seconds |
| Ex. 8 | No | — |
| Ex. 9 | No | Just Very Wet Bubbles produced lasting <10 seconds |
| Ex. 10 | No | — |
| Ex. 11 | No | — |
| Ex. 12 | No | — |
| Ex. 13 | Yes | Quick fast breaking foam lasts more than a minute |
| Ex. 14 | Yes | Very good puff creamy and soft lasts minutes |
| Ex. 15 | Yes | Very good puff creamy and soft lasts minutes |
| Ex. 16 | Yes | Quick fast breaking foam lasts more than a minute |
| Ex. 17 | Yes | Very good puff creamy and soft lasts minutes |
| Ex. 18 | Yes | Good puff creamy and soft lasts minutes |
| Ex. 19 | Yes | Quick fast breaking foam lasts more than a 10 secs |
| Ex. 20 | Yes | — |
| Ex. 21 | Yes | Runny watery foam which lasts more than 45 secs |
| Ex. 22 | Yes | Quick fast breaking foam lasts more than a 10 secs |
| Ex. 23 | Yes | Runny watery foam which lasts more than 20 secs |
| Ex. 24 | Yes | — |
| Ex. 25 | Yes | Runny watery foam which lasts more than 20 secs |
| Ex. 26 | Yes | Runny foam which lasts more than 20 secs |
| Ex. 27 | Yes | Quick fast breaking foam lasts more than a 45 secs |
| Ex. 28 | No | Quick fast breaking foam lasts more than a 45 secs |
| Ex. 29 | Yes | Very good creamy and soft lasts more than a minute |
| Ex. 30 | Yes | Good creamy and soft lasts more than a minute |
| Ex. 31 | Yes | Quick fast breaking foam lasts more than a 45 secs |
| Ex. 32 | No | — |
| Ex. 33 | No | Quick fast breaking foam lasts more than a minute |
| Ex. 34 | No | Good creamy and soft lasts more than a minute |
| Ex. 35 | No | Very good creamy and soft lasts more than a minute |
| Ex. 36 | No | Very good creamy and soft lasts minutes |
| Ex. 37 | Yes | Quick fast breaking foam lasts more than a 20 secs |
| Ex. 38 | No | — |
| Ex. 39 | No | — |
| Ex. 40 | No | — |
| Ex. 41 | No | — |
| Ex. 42 | No | — |
| Ex. 43 | No | — |
| Ex. 44 | No | — |
| Ex. 45 | No | — |
| Ex. 46 | No | — |
| Ex. 47 | No | — |
| Ex. 48 | No | — |
| Ex. 49 | Yes | Runny watery foam which lasts more than a 45 secs |
| Ex. 50 | Yes | Runny watery foam which lasts more than a 45 secs |
| Ex. 51 | Yes | Runny watery foam which lasts more than a 45 secs |
| Ex. 52 | Yes | Runny watery foam which lasts more than a 45 secs |

Examples 53-63

| INGREDIENTS | 53 | 54 | 55 | 56 | 57 | 58 | 59 | 60 | 61 | 62 | 63 |
|---|---|---|---|---|---|---|---|---|---|---|---|
| 1,3-butylene glycol | 0.43 | 0.43 | 1 | 1 | 1 | 0.43 | 0.43 | 1 | 1 | 1 | 0.43 |
| Ethanol | 62 | 52 | 52.2 | 62.2 | 42.2 | 62 | 52 | 52.2 | | 42.2 | 62 |
| Benzalkonium Chloride | | | | | | 0.1 | 0.1 | 0.1 | 0.1 | 0.1 | |
| Dimethyl Ammonium Chloride | | | | | | | | | | | 0.1 |
| PEG 17-Dimethicone | 1 | 1 | 1 | 1 | 1 | 1 | 1 | 1 | 1 | 1 | 1 |
| Glycerine | 0.9 | 0.9 | 0.5 | 0.5 | 0.5 | 0.9 | 0.9 | 0.5 | 0.5 | 0.5 | 0.9 |
| Cocoglucoside & Glyceryl Oleate | 0.08 | 0.08 | | | | 0.08 | 0.08 | | | | 0.08 |
| DEA C8–C18 Perfluoroalkylethyl Phosphate | | | | | | | | | | | |
| Ammonium C6–C16 Perfluoroalkylethyl Phosphate | 0.5 | 0.5 | 0.3 | 0.3 | 0.3 | 0.3 | 0.3 | 0.3 | 0.3 | 0.3 | 0.5 |
| Cetrimonium Chloride | | | | | | | | | | | |
| n-Propyl alcohol | 2 | 10 | 10 | | 20 | 2 | 10 | 10 | 62.2 | 20 | 2 |
| Propylene glycol | | | | 0.5 | 0.5 | | | 0.5 | 0.5 | 0.5 | |
| Purified Water | 33.1 | 36.1 | 34.6 | 34.6 | 34.6 | 33.2 | 35.2 | 34.5 | 34.5 | 34.5 | 33 |

Examples 64-73

| INGREDIENTS | 64 | 65 | 66 | 67 | 68 | 69 | 70 | 71 | 72 | 73 | 64 |
|---|---|---|---|---|---|---|---|---|---|---|---|
| 1,3-butylene glycol | 0.43 | 0.43 | 1 | 1 | 1 | 0.43 | 0.43 | 0.43 | 0.43 | 0.43 | 0.43 |
| Ethanol | 62 | 62 | 52.2 | 52.2 | 52.2 | 62 | 52 | 62 | 62 | 62 | 62 |
| Benzalkonium Chloride | | | | | | | | | | | |
| Dimethyl Ammonium Chloride | 0.5 | 1 | 0.1 | 0.1 | 1 | | | | | | 0.5 |
| PEG 17-Dimethicone | 1 | 1 | 1 | 1 | 1 | 1 | 1.5 | 1 | 1 | 1 | 1 |
| Glycerine | 0.9 | 0.9 | 0.5 | 0.5 | 0.5 | 0.9 | 0.9 | 0.9 | 0.9 | 0.9 | 0.9 |
| Cocoglucoside & Glyceryl Oleate | 0.08 | 0.08 | | | | 0.08 | | 0.08 | 0.08 | 0.08 | 0.08 |
| DEA C8–C18 Perfluoroalkylethyl Phosphate | | | | | | | 0.3 | 0.5 | 0.5 | 0.5 | |
| Ammonium C6–C16 Perfluoroalkylethyl Phosphate | 0.5 | 0.5 | 0.3 | 0.3 | 0.3 | 0.5 | 0.3 | | | | 0.5 |
| Cetrimonium Chloride | | | | | | | | 0.05 | 0.1 | 0.05 | |
| n-Propyl alcohol | 2 | 2 | 10 | 10 | 10 | 2 | 10 | 2 | 2 | 2 | 2 |
| Propylene glycol | | | 0.5 | 0.5 | 0.5 | | | | | | |
| Purified Water | 32.6 | 32.1 | 34.5 | 34.5 | 33.6 | 33.1 | 35 | 33 | 33 | 33 | 32.6 |

Example 74-84

| INGREDIENTS | 74 | 75 | 76 | 77 | 78 | 79 | 80 | 81 | 82 | 83 | 84 |
|---|---|---|---|---|---|---|---|---|---|---|---|
| 1,3-butylene glycol | 0.43 | 0.43 | 0.43 | 0.43 | 0.43 | 0.43 | 0.43 | 0.43 | 0.43 | 0.43 | 0.43 |
| Ethanol | 52 | 62 | 62 | 52 | 52 | 62 | 62 | 52 | 52 | 62 | 62 |
| Glycerine | 0.9 | 0.9 | 0.9 | 0.9 | 0.9 | 0.9 | 0.9 | 0.9 | 0.9 | 0.9 | 0.9 |
| Cocoglucoside & Glyceryl Oleate | 0.08 | 0.08 | 0.08 | 0.08 | 0.08 | 0.08 | 0.08 | 0.08 | 0.08 | 0.08 | 0.08 |
| Bis-PEG 17 Dimethicone | | 5.5 | 5.5 | | | 5.5 | 5.5 | | | 5.5 | 5.5 |
| Bis-PEG 12 Dimethicone | 4.8 | | | 4.8 | 4.8 | | | 4.8 | 4.8 | | |
| Cetrimonium Chloride | 0.1 | | | | | | | | | | |
| Dihydroxypropyl PEG-5 Linoleammonium Chloride | | 0.05 | 0.1 | 0.05 | 0.1 | 0.1 | | | | | |
| Behenoyl PG-Trimonium Chloride | | | | | | | 0.05 | 0.1 | 0.05 | 0.1 | |
| Behenamidopropyl Dimethylamine | | | | | | | | | | 0.05 | 0.1 |
| Behentrimonium Chloride | | | | | | | | | | | |
| Cetearyl Alcohol and Behentrimonium Chloride | | | | | | | | | | | |
| n-Propyl alcohol | 10 | 2 | 2 | 10 | 10 | 2 | 2 | 10 | 10 | 2 | 2 |
| Propylene glycol | | | | | | | | | | | |
| Purified Water | 31.7 | 29 | 29 | 31.7 | 31.7 | 28.9 | 29 | 31.7 | 31.7 | 29 | 29 |

Example 85-94

| INGREDIENTS | 85 | 86 | 87 | 88 | 89 | 90 | 91 | 92 | 93 | 94 |
|---|---|---|---|---|---|---|---|---|---|---|
| 1,3-butylene glycol | 0.43 | 0.43 | 0.43 | 0.43 | 0.43 | 0.43 | 0.43 | 0.43 | 0.43 | 0.43 |
| Ethanol | 52 | 52 | 62 | 62 | 52 | 52 | 62 | 62 | 52 | 52 |
| Glycerine | 0.9 | 0.9 | 0.9 | 0.9 | 0.9 | 0.9 | 0.9 | 0.9 | 0.9 | 0.9 |
| Cocoglucoside & Glyceryl Oleate | 0.08 | 0.08 | 0.08 | 0.08 | 0.08 | 0.08 | 0.08 | 0.08 | 0.08 | 0.08 |
| Bis-PEG 17 Dimethicone | | | 5.5 | 5.5 | | | 5.5 | 5.5 | | |

-continued

| INGREDIENTS | 85 | 86 | 87 | 88 | 89 | 90 | 91 | 92 | 93 | 94 |
|---|---|---|---|---|---|---|---|---|---|---|
| Bis-PEG 12 Dimethicone | 4.8 | 4.8 | | | 4.8 | 4.8 | | | 4.8 | 4.8 |
| Cetrimonium Chloride | | | | | | | | | | |
| Dihydroxypropyl PEG-5 Linoleammonium Chloride | | | | | | | | | | |
| Behenoyl PG-Trimonium Chloride | | | | | | | | | | |
| Behenamidopropyl Dimethylamine | 0.05 | 0.1 | | | | | | | | |
| Behentrimonium Chloride | | | 0.5 | 0.1 | 0.05 | 0.1 | | | | |
| Cetearyl Alcohol and Behentrimonium Chloride | | | | | | | 0.05 | 0.1 | 0.05 | 0.1 |
| n-Propyl alcohol | 10 | 10 | 2 | 2 | 10 | 10 | 2 | 2 | 10 | 10 |
| Propylene glycol | | | | | | | | | | |
| Purified Water | 31.7 | 31.7 | 28.6 | 29 | 31.7 | 31.7 | 29 | 29 | 31.7 | 31.7 |

Examples 95-115

| INGREDIENTS | 95 | 96 | 97 | 98 | 99 | 100 | 101 | 102 | 103 | 104 | 105 |
|---|---|---|---|---|---|---|---|---|---|---|---|
| Dimethicone PEG-8 | | | | | | | 1 | 1.5 | 2 | 1 | 1.5 |
| Bis-PEG/PPG 18/6 Dimethicone | 1 | 1.5 | 2 | 1 | 1.5 | 2 | | | | | |
| Ethanol | | | | | | | | | | | |
| PEG-17 Dimethicone | | | | | | | | | | 1 | 1 |
| Glycerine | | | 1 | 1 | 1 | | | | | | |
| Isopropyl Alcohol | 70 | 70 | 70 | 70 | 70 | 70 | 70 | 70 | 70 | 70 | 70 |
| n-Propyl Alcohol | | | | | | | | | | | |
| Purified Water | 29 | 28.5 | 28 | 28 | 27.5 | 27 | 29 | 28.5 | 28 | 28 | 27.5 |

| INGREDIENTS | 106 | 107 | 108 | 109 | 110 | 111 | 112 | 113 | 114 | 115 |
|---|---|---|---|---|---|---|---|---|---|---|
| Dimethicone PEG-8 | 2 | | | | | | | 1 | 1.5 | 2 |
| Bis-PEG/PPG 18/6 Dimethicone | | 1 | 1.5 | 2 | 1 | 1.5 | 2 | | | |
| Ethanol | | 55 | 55 | 55 | 55 | 55 | 55 | 55 | 55 | 55 |
| PEG-17 Dimethicone | 1 | | | | | | | | | |
| Glycerine | | | | | 1 | 1 | 1 | | | |
| Isopropyl Alcohol | 70 | | | | | | | | | |
| n-Propyl Alcohol | | 10 | 10 | 10 | 10 | 10 | 10 | 10 | 10 | 10 |
| Purified Water | 27 | 34 | 33.5 | 33 | 33 | 32.5 | 32 | 34 | 33.5 | 33 |

Examples 116-136

| INGREDIENTS | 116 | 117 | 118 | 119 | 120 | 121 | 122 | 123 | 124 | 125 | 126 |
|---|---|---|---|---|---|---|---|---|---|---|---|
| Dimethicone PEG-8 | 1 | 1.5 | 2 | | | | | | | 1 | 1.5 |
| Bis-PEG/PPG 18/6 Dimethicone | | | | 1 | 1.5 | 1 | 1 | 1.5 | 2 | | |

-continued

| Ingredient | | | | | | | | | | | |
|---|---|---|---|---|---|---|---|---|---|---|---|
| Ethanol | 55 | 55 | 55 | 65 | 65 | 65 | 65 | 65 | 65 | 65 | 65 |
| PEG-17 Dimethicone | | | | | | | | | | | |
| Glycerine | 1 | 1 | 1 | | | | 1 | 1 | 1 | | |
| n-Propyl Alcohol | 10 | 10 | 10 | | | | | | | | |
| Purified Water | 33 | 32.5 | 32 | 34 | 33.5 | 34 | 33 | 32.5 | 32 | 34 | 33.5 |

| INGREDIENTS | 127 | 128 | 129 | 130 | 131 | 132 | 133 | 134 | 135 | 136 |
|---|---|---|---|---|---|---|---|---|---|---|
| Dimethicone PEG-8 | 2 | 1 | 1.5 | 2 | | | | | | |
| Bis-PEG/PPG 18/6 Dimethicone | | | | | 1 | 1.5 | 2 | 1 | 1.5 | 2 |
| Ethanol | 65 | 65 | 65 | 65 | | | | | | |
| PEG-17 Dimethicone | | | | | | | | | | |
| Glycerine | | 1 | 1 | 1 | | | | 1 | 1 | 1 |
| n-Propyl Alcohol | | | | | 62 | 62 | 62 | 62 | 62 | 62 |
| Purified Water | 33 | 33 | 32.5 | 32 | 37 | 36.5 | 36 | 36 | 35.5 | 35 |

Examples 137-156

| INGREDIENTS | 137 | 138 | 139 | 140 | 141 | 142 | 143 | 144 | 145 | 146 |
|---|---|---|---|---|---|---|---|---|---|---|
| Cetrimonium Chloride | | | | | | | | | | |
| Dimethicone PEG-8 | 1 | 1.5 | 2 | 1 | 1.5 | 2 | | | | |
| Bis-PEG/PPG 18/6 Dimethicone | | | | | | | | | | 1.5 |
| Ethanol | | | | | | | 55 | 55 | 55 | |
| PEG-17 Dimethicone | | | | | | | | | | |
| Glycerine | | | | 1 | 1 | 1 | 1 | 1 | 1 | |
| n-Propyl Alcohol | 62 | 62 | 62 | 62 | 62 | 62 | 10 | 10 | 10 | 62 |
| Bis-PEG 12 Dimethicone | | | | | | | 3 | 4 | 5 | |
| Dihydroxypropyl PEG-5 Linoleammonium Chloride | | | | | | | | | | 0.1 |
| Purified Water | 37 | 36.5 | 36 | 36 | 35.5 | 35 | 31 | 30 | 29 | 36.4 |

| INGREDIENTS | 147 | 148 | 149 | 150 | 151 | 152 | 153 | 154 | 155 | 156 |
|---|---|---|---|---|---|---|---|---|---|---|
| Cetrimonium Chloride | 0.1 | | | | | 0.1 | | | | |
| Dimethicone PEG-8 | | | | 0.5 | | | | | | |
| Bis-PEG/PPG 18/6 Dimethicone | 5 | 5 | 1 | 2 | 1.5 | 3 | 3 | | | |
| Ethanol | | | 61 | 61 | 61 | 61 | 61 | 55 | 55 | 55 |
| PEG-17 Dimethicone | | | | | | | | | | |
| Glycerine | | | | | | | | | | |
| n-Propyl Alcohol | 62 | 62 | | | | | | 10 | 10 | 10 |
| Bis-PEG 12 Dimethicone | | | | | | | | 1 | 1.5 | 2 |
| Dihydroxypropyl PEG-5 Linoleammonium Chloride | | 0.1 | | | | 0.1 | | | | |
| Purified Water | 37.9 | 37.9 | 38 | 37 | 37 | 35.9 | 35.9 | 34 | 33.5 | 33 |

Examples 157-167

| INGREDIENTS | 157 | 158 | 159 | 160 | 161 | 162 | 163 | 164 | 165 | 166 | 167 |
|---|---|---|---|---|---|---|---|---|---|---|---|
| 1,3 Butylene Glycol | | | | | | | | | | | |
| Alcohol | | | | | | | | | | | |
| Behenamidopropyl Dimethylamine | | | | | | | | | | | |
| Behentrimonium Chloride | | | | | | | | | | | |
| Cetrimonium Chloride | 0.1 | | | | 0.1 | | | | | | 0.1 |
| Bis-PEG/PPG 18/6 Dimethicone | | | | | | | | | | | |
| Ethanol | 55 | 55 | 61 | 61 | 61 | 61 | 61 | | | | |
| Glycerine | | | | | | | | | | | |
| Cocoglucoside Glyceryl Oleate | | | | | | | | | | | |
| n-Propyl Alcohol | 10 | 10 | | | | | | 62 | 62 | 62 | 62 |
| Bis-PEG 12 Dimethicone | 1.5 | 1.5 | 1 | 1.5 | 2 | 1.5 | 1.5 | 1 | 1.5 | 2 | 1.5 |

| INGREDIENTS | 157 | 158 | 159 | 160 | 161 | 162 | 163 | 164 | 165 | 166 | 167 |
|---|---|---|---|---|---|---|---|---|---|---|---|
| Dihydroxypropyl PEG-5 Linoleammonium Chloride | | 0.1 | | | | | 0.1 | | | | |
| Purified Water | 33.4 | 33.4 | 38 | 37.5 | 37 | 37.4 | 37.4 | 37 | 36.5 | 36 | 36.4 |

Examples 168-177

| INGREDIENTS | 168 | 169 | 170 | 171 | 172 | 173 | 174 | 175 | 176 | 177 |
|---|---|---|---|---|---|---|---|---|---|---|
| 1,3 Butylene Glycol | | 4.3 | 4.3 | 4.3 | 4.3 | 4.3 | 4.3 | 4.3 | | |
| Alcohol | | 62 | 62 | 62 | 62 | 62 | 62 | 62 | | |
| Behenamidopropyl Dimethylamine | | | | | | | | | 0.1 | |
| Behentrimonium Chloride | 0.1 | | | | | | | | | 0.1 |
| Cetrimonium Chloride | | | | | | | | | | |
| Bis-PEG/PPG 18/6 Dimethicone | | | | | | 1 | 1.5 | 2 | | |
| Ethanol | | | | | | | | | 61 | 61 |
| Glycerine | | 0.9 | 0.9 | 0.9 | 0.9 | 0.9 | 0.9 | 0.9 | | |
| Cocoglucoside Glyceryl Oleate | | 0.08 | 0.08 | 0.08 | 0.08 | 0.08 | 0.08 | 0.08 | | |
| n-Propyl Alcohol | 62 | 2 | 2 | 2 | 2 | 2 | 2 | 2 | | |
| Bis-PEG 12 Dimethicone | 1.5 | | 1 | 1.5 | 2 | | | | 2 | 2 |
| Dihydroxypropyl PEG-5 Linoleammonium Chloride | | | | | | | | | | |
| Purified Water | 36.4 | 30.7 | 29.7 | 29.2 | 28.7 | 29.7 | 29.2 | 28.7 | 36.9 | 36.9 |

Examples 178-188

| INGREDIENTS | 178 | 179 | 180 | 181 | 182 | 183 | 184 | 185 | 186 | 187 | 188 |
|---|---|---|---|---|---|---|---|---|---|---|---|
| 1,3-butylene glycol | | | 4.3 | 4.3 | 4.3 | 4.3 | | 0.43 | 0.43 | 0.43 | 0.43 |
| Ethanol | | | 62 | 62 | 62 | 62 | | 70 | 70 | 70 | 70 |
| Behenoyl PG-Trimonium Chloride | | 0.1 | | | | | | | | | |
| Cetearyl Alcohol &Behentrimonium Chloride | 0.1 | | | | | | | | | | |
| Behentrimonium Chloride | | | | | | | | | | | |
| Cetrimonium Chloride | | | | | | | | 0.1 | 0.1 | 0.1 | |
| Dimethicone PEG-8 | | | | | 0.5 | 0.5 | | 0.5 | | 0.5 | |
| Bis-PEG/PPG 15/15 Dimethicone | | | | | | | | | | | |
| Bis-PEG/PPG 18/6 Dimethicone | | | 0.5 | 0.75 | | 2 | | | | | |
| Ethanol | 61 | 61 | | | | | | | | | |
| PEG-17 Dimethicone | | | | | | | | | | | |
| Glycerine | | | 0.9 | 0.9 | 0.9 | 0.9 | | 0.9 | 0.9 | 0.9 | 0.9 |
| Isopropyl Alcohol | | | | | | | | | | | |
| Cocoglucoside & Glyceryl Oleate | | | 0.08 | 0.08 | 0.08 | 0.08 | | 0.08 | 0.08 | 0.08 | 0.08 |
| n-Propyl Alcohol | | | 2 | 2 | 2 | 2 | | 2 | 2 | | |
| PEG-200 Hydrogenated Glyceryl Palmate | | | | | | | | | | | |
| Bis-PEG 12 Dimethicone | 2 | 2 | 0.5 | 0.75 | 2 | | | 2.5 | 2.5 | 2.5 | 2.5 |
| Purified Water | 36.9 | 36.9 | 29.7 | 29.2 | 28.2 | 28.2 | 100 | 23.5 | 24 | 25.5 | 26.1 |

Examples 189-198

| INGREDIENTS | 189 | 190 | 191 | 192 | 193 | 194 | 195 | 196 | 197 | 198 |
|---|---|---|---|---|---|---|---|---|---|---|
| 1,3-butylene glycol | | 0.43 | 0.43 | 0.43 | 0.43 | 0.43 | 0.43 | | | |
| Ethanol | 55 | 62 | 62 | 70 | 70 | 70 | 70 | | | |
| Behenoyl PG-Trimonium Chloride | | | | | | | | | | |
| Cetearyl Alcohol &Behentrimonium Chloride | | | | | | | | | | |
| Behentrimonium Chloride | 0.1 | 0.1 | 0.1 | | | | | | | |
| Cetrimonium Chloride | 0.1 | 0.1 | 0.1 | 0.1 | 0.1 | 0.1 | 0.1 | | | |
| Dimethicone PEG-8 | 2 | | | | | | | | | |
| Bis-PEG/PPG 15/15 Dimethicone | | | | | 2.5 | 2.5 | | 2 | 2 | |
| Bis-PEG/PPG 18/6 Dimethicone | | | | | | | | | | |
| Ethanol | | | | | | | | 61 | 55 | 61 |
| PEG-17 Dimethicone | | | | | | | | 2 | | |
| Glycerine | | 0.9 | 0.9 | 0.9 | 0.9 | 0.9 | 0.9 | | | |
| Isopropyl Alcohol | | | | | | | | | | |
| Cocoglucoside & Glyceryl Oleate | | 0.08 | 0.08 | 0.08 | 0.08 | 0.08 | 0.08 | | | |
| n-Propyl Alcohol | 10 | 2 | 2 | | | | | | 10 | |
| PEG-200 Hydrogenated Glyceryl Palmate | | | | 0.1 | 0.5 | 0.5 | 0.5 | | | |
| Bis-PEG 12 Dimethicone | | 2.5 | 2 | 2.5 | 2.5 | | | | | |
| Purified Water | 32.8 | 31.9 | 32.4 | 25.9 | 25.5 | 25.5 | 25.5 | 37 | 33 | 37 |

Examples 199-219

| INGREDIENTS | 199 | 200 | 201 | 202 | 203 | 204 | 205 | 206 | 207 | 208 | 209 |
|---|---|---|---|---|---|---|---|---|---|---|---|
| 1,3 Butylene Glycol | | | 0.43 | | 0.43 | | | | | | |
| Cetearyl Alcohol and Behentrimonium Chloride | | | | | 1 | | | | | | |
| Behentrimonium Chloride | | | 0.1 | | 0.1 | | | | | | |
| Bis-PEG/PPG 18/6 Dimethicone | | | | 1 | | | | | | | |
| Ethanol | 55 | 55 | 70 | 55 | 70 | 55 | 55 | 55 | 55 | 55 | 55 |
| PEG-17 Dimethicone | 2 | 1 | | 1 | | 2 | | | 1 | | 1 |
| Glycerine | | | 0.9 | | 0.9 | | | | | | |
| Cocoglucoside Glyceryl Oleate | | | 0.08 | | 0.08 | | | | | | |
| n-Propyl Alcohol | 10 | 10 | | 10 | | 10 | 10 | 10 | 10 | 10 | 10 |
| PEG-200 Hydrogenated Glyceryl Palmate | | 1 | | | | | | | | | |
| Bis-PEG 20 Dimethicone | | | | | | | | 2 | | 1 | 1 |
| Bis-PEG 12 Dimethicone | | 1 | 2.5 | | 2.5 | | | 2 | 1 | 1 | |
| Purified Water | 43 | 43 | 25 | 43 | 25 | 43 | 43 | 43 | 43 | 43 | 43 |

| INGREDIENTS | 210 | 211 | 212 | 213 | 214 | 215 | 216 | 217 | 218 | 219 |
|---|---|---|---|---|---|---|---|---|---|---|
| 1,3 Butylene Glycol | | | | | | | | | | |
| Cetearyl Alcohol and Behentrimonium Chloride | | | | | | | | | | |
| Behentrimonium Chloride | | | | | | | | | | |
| Bis-PEG/PPG 18/6 Dimethicone | | | | | | | | | | |
| Ethanol | 62 | 62 | 62 | 62 | 62 | 62 | 70 | 70 | 70 | 70 |
| PEG-17 Dimethicone | 2 | | | 1 | | 1 | 2 | | | 1 |
| Glycerine | | | | | | | | | | |
| Cocoglucoside Glyceryl Oleate | | | | | | | | | | |
| n-Propyl Alcohol | 2 | 2 | 2 | 2 | 2 | 2 | | | | |
| PEG-200 Hydrogenated Glyceryl Palmate | | | | | | | | | | |
| Bis-PEG 20 Dimethicone | | 2 | | | 1 | 1 | | 2 | | |
| Bis-PEG 12 Dimethicone | | | 2 | 1 | 1 | | | | 2 | 1 |
| Purified Water | 36 | 36 | 36 | 36 | 36 | 36 | 28 | 28 | 28 | 28 |

Examples 220-230

| INGREDIENTS | 220 | 221 | 222 | 223 | 224 | 225 | 226 | 227 | 228 | 229 | 230 |
|---|---|---|---|---|---|---|---|---|---|---|---|
| PEG-8 Dimethicone |  |  | 0.01 | 0.01 | 0.05 | 0.01 | 0.01 | 0.05 | 0.01 | 0.01 | 0.01 |
| Ethanol | 70 | 70 | 62 | 62 | 62 | 70 | 70 | 70 | 60 | 60 | 60 |
| PEG-17 Dimethicone |  | 1 |  |  |  |  |  |  |  |  |  |
| n-Propyl Alcohol |  |  | 2 | 2 | 2 | 2 | 2 | 2 | 10 | 10 | 10 |
| Bis-PEG 20 Dimethicone | 1 | 1 |  |  |  |  |  |  |  |  |  |
| Bis-PEG-12 Dimethicone | 1 |  | 1 | 1 | 1 | 1 | 1 | 1 | 1 | 1 | 1 |
| Purified Water | 28 | 28 | 35 | 35 | 35 | 27 | 27 | 27 | 29 | 29 | 29 |

Examples 231-240

| INGREDIENTS | 231 | 232 | 233 | 234 | 235 | 236 | 237 | 238 | 239 | 240 |
|---|---|---|---|---|---|---|---|---|---|---|
| PEG-8 Dimethicone | 0.01 | 0.01 | 0.05 | 0.01 | 0.01 | 0.05 | 0.01 | 0.01 | 0.05 | 0.01 |
| Ethanol |  |  |  | 55 | 55 | 55 | 65 | 65 | 65 | 61 |
| PEG-17 Dimethicone |  |  |  |  |  |  |  |  |  |  |
| n-Propyl Alcohol | 60 | 60 | 60 | 10 | 10 | 10 | 10 | 10 | 10 | 39 |
| Bis-PEG 20 Dimethicone |  |  |  |  |  |  |  |  |  |  |
| Bis-PEG-12 Dimethicone | 1 | 1 | 1 | 1 | 1 | 1 | 1 | 1 | 1 | 1 |
| Purified Water | 39 | 39 | 39 | 34 | 34 | 34 | 24 | 24 | 24 | −1 |

Examples 241-251

| INGREDIENTS | 241 | 242 | 243 | 244 | 245 | 246 | 247 | 248 | 249 | 250 | 251 |
|---|---|---|---|---|---|---|---|---|---|---|---|
| PEG-8-Dimethicone | 0.01 | 0.05 |  |  |  |  |  |  |  |  |  |
| Bis-PEG/PPG 18/6 Dimethicone |  |  |  |  |  |  |  |  | 1 | 1 | 1 |
| Ethanol | 61 | 61 | 55 | 65 | 61 |  | 70 | 62 | 60 | 65 | 65 |
| DEA C8–C18 Perfluoroalkylethyl Phosphate |  |  |  |  |  |  |  |  |  |  |  |
| Ammonium C6–C16 Perfluoroalkylethyl Phosphate |  |  |  |  |  |  |  |  | 1 | 1 | 1 |
| Cetrimonium Chloride |  |  |  |  |  |  |  |  |  |  |  |
| Dihydroxypropyl PEG-5 Linoleammonium Chloride |  |  |  |  |  |  |  |  |  |  |  |
| n-Propyl Alcohol |  |  | 10 | 10 |  | 60 | 2 | 2 | 10 | 10 | 10 |
| Bis PEG 12-Dimethicone | 1 | 1 | 1 | 1 | 1 | 1 | 1 | 1 | 1 | 1 |  |
| Purified Water | 38 | 38 | 34 | 24 | 38 | 39 | 27 | 35 | 27 | 22 | 23 |

Examples 252-261

| INGREDIENTS | 252 | 253 | 254 | 255 | 256 | 257 | 258 | 259 | 260 | 261 |
|---|---|---|---|---|---|---|---|---|---|---|
| PEG-8-Dimethicone |  |  |  |  |  |  |  |  |  |  |
| Bis-PEG/PPG 18/6 Dimethicone | 1 | 1 |  | 1.5 |  |  |  |  |  |  |
| Ethanol | 65 | 65 | 65 | 65 | 61 | 61 | 61 | 61 | 61 | 61 |
| DEA C8–C18 Perfluoroalkylethyl Phosphate | 1 | 1 |  |  |  |  |  |  |  |  |
| Ammonium C6–C16 Perfluoroalkylethyl Phosphate |  |  |  |  |  |  |  |  |  |  |
| Cetrimonium Chloride |  |  |  |  | 0.1 | 0.5 | 1 | 0.1 | 0.5 | 1 |
| Dihydroxypropyl PEG-5 Linoleammonium Chloride |  |  |  |  |  |  |  | 0.1 | 0.5 | 1 |
| n-Propyl Alcohol | 10 | 10 | 10 | 10 |  |  |  |  |  |  |
| Bis PEG 12-Dimethicone |  | 1 | 1.5 |  | 1 | 1 | 1 |  |  |  |
| Purified Water | 23 | 22 | 23.5 | 23.5 | 37.9 | 37.5 | 37 | 38.8 | 38 | 37 |

Examples 262-272

| INGREDIENTS | 262 | 263 | 264 | 265 | 266 | 267 | 268 | 269 | 270 | 271 | 272 |
|---|---|---|---|---|---|---|---|---|---|---|---|
| Behenyl PG-Trimonium Chloride | | | | | | | | | | | |
| Cetearyl Alcohol and Behentrimonium Chloride | | | | | | | | | | | |
| Polyethylene Glycol 600 | | | | 0.1 | 0.5 | 1 | | | | | |
| PEG-7 Glyceryl Cocoate | | | | | | | | | | | |
| Ethanol | 61 | 61 | 61 | 61 | 61 | 61 | 61 | 61 | 61 | 61 | 61 |
| Cocoglucoside & Glyceryl Oleate | | | | | | | | | | 0.1 | 0.5 |
| Polyethylene Glycol | 0.2 | 0.5 | 1 | | | | | | | | |
| PEG-200 Hydrogenated Glyceryl Palmate | | | | | | | | 0.1 | 0.5 | 1 | |
| Bis-PEG 12 Dimethicone | 1 | 1 | 1 | 1 | 1 | 1 | 1 | 1 | 1 | 1 | 1 |
| Purified Water | 37.8 | 37.5 | 37 | 37.9 | 37.5 | 37 | 37.9 | 37.5 | 37 | 37.9 | 37.5 |

Examples 273-282

| INGREDIENTS | 273 | 274 | 275 | 276 | 277 | 278 | 279 | 280 | 281 | 282 |
|---|---|---|---|---|---|---|---|---|---|---|
| Behenyl PG-Trimonium Chloride | | | | 0.1 | 0.5 | 1 | | | | |
| Cetearyl Alcohol and Behentrimonium Chloride | | | | | | | 0.1 | 0.5 | 1 | |
| Polyethylene Glycol 600 | | | | | | | | | | |
| PEG-7 Glyceryl Cocoate | | | | | | | | | | 0.1 |
| Ethanol | 61 | 61 | 61 | 61 | 61 | 61 | 61 | 61 | 61 | 61 |
| Cocoglucoside & Glyceryl Oleate | 1 | | | | | | | | | |
| Polyethylene Glycol | | | | | | | | | | |
| PEG-200 Hydrogenated Glyceryl Palmate | | | | | | | | | | |
| Bis-PEG 12 Dimethicone | 1 | 2 | 3 | 1 | 1 | 1 | 1 | 1 | 1 | 1 |
| Purified Water | 37 | 37 | 36 | 37.9 | 37.5 | 37 | 37.9 | 37.5 | 37 | 37.9 |

Examples 283-293

| INGREDIENTS | 283 | 284 | 285 | 286 | 287 | 288 | 289 | 290 | 291 | 292 | 293 |
|---|---|---|---|---|---|---|---|---|---|---|---|
| Behenyl PG-Trimonium Chloride | | | 0.2 | 0.25 | 0.2 | 0.25 | | | | 0.2 | 0.2 |
| Cetearyl Alcohol and Behentrimonium Chloride | | | 0.3 | 0.4 | 0.3 | 0.4 | | | | 0.3 | 0.3 |
| PEG-7 Glyceryl Cocoate | 0.5 | 1 | 0.15 | 0.2 | 0.15 | 0.2 | | | | 0.15 | 0.15 |
| PEG-PPG 20/6 Dimethicone | | | | | | | | | 1 | | |
| PEG 4-Dimethicone | | | | | | | 1 | | | | |
| PEG-8-Dimethicone | | | | | | | | 1 | | | |
| Ethanol | 61 | 61 | 61 | 61 | 65 | 65 | 65 | 65 | 65 | 61 | 61 |
| Cocoglucoside & Glyceryl Oleate | | | 0.2 | 0.25 | 0.2 | 0.25 | | | | 0.2 | 0.2 |
| Cetrimonium Chloride | | | 0.1 | 0.2 | 0.1 | 0.2 | | | | 0.1 | 0.1 |
| Dihydroxypropyl PEG-5 Linoleammonium Chloride | | | 0.4 | 0.5 | 0.4 | 0.5 | | | | 0.4 | 0.4 |
| n-Propyl Alcohol | | | | | 10 | 10 | 10 | 10 | 10 | | |
| PEG-200 Hydrogenated Glyceryl Palmate | | | 0.15 | 0.2 | 0.15 | 0.2 | | | | 0.15 | 0.15 |
| Bis-PEG 12 Dimethicone | 1 | 1 | 2 | 2 | 2 | 3 | | | | 1.5 | 1 |
| Purified Water | 37.5 | 37 | 35.5 | 35 | 21.5 | 20 | 24 | 24 | 24 | 36 | 36.5 |

What is claimed is:

1. An alcohol disinfecting composition, comprising;
   a) an alcohol $C_{1-4}$, or mixtures thereof, present in an amount between about 60% to about 80% v/v of the total composition;
   b) at least one effective physiologically acceptable silicone-based surface active agent, which includes a lipophilic chain containing a silicone backbone, for foaming present in an amount from about 0.01% to about 10.0% by weight of the total composition;
   c) a foam stabilizing agent present in an amount from about 0.01 to about 12.0% by weight of the total composition;
   d) one or more moisturizers, emollients, lipid layer enhancers, or combinations thereof present in an amount from about 0.05 to about 5.0% by weight of the total composition; and
   e) water in an amount to balance the total composition to 100% by weight,
   said alcohol composition optionally including no more than 1% by weight of at least one additional surfactant for adjusting properties of the foam produced from the composition,
   wherein the composition is mixed with air at low pressure to form a foam.

2. The alcohol disinfecting composition according to claim 1 wherein the silicone-based surfactant is Bis-PEG-20 dimethicone.

3. The alcohol disinfecting composition according to claim 1 wherein the silicone-based surfactant is Bis-PEG-17 dimethicone.

4. The alcohol disinfecting composition according to claim 1 wherein the silicone-based surfactant is Bis-PEG-12 dimethicone.

5. The alcohol disinfecting composition according to claim 1 wherein the silicone-based surfactant is a polyether-modified polysiloxane.

6. The alcohol disinfecting composition according to claim 1 wherein the silicone-based surfactant is a polysiloxane betaine.

7. The composition according to claim 1 wherein the silicone-based surfactant is a mixture of two or more of the silicone-based surfactants selected from the group consisting of Bis-PEG-20 dimethicone, Bis-PEG-17 dimethicone, Bis-PEG-12 dimethicone, 3-(3-hydroxypropyl)-heptamethyltrisiloxaneethoxylated acetate, polyether-modified polysiloxane and polysiloxane betaine.

8. The alcohol disinfecting composition according to claim 1 wherein the foam stabilizing agent is selected from the group consisting of
   lactic acid esters of monoglycerides,
   cationic emulsifiers,
   quaternary ammonium compounds,
   triquaternized stearic phospholipid complex,
   hydroxystearamide propyltriamine salts,
   lactic acid monoglycerides,
   food emulsifiers selected from the group consisting of glyceryl monostearate, propylene glycol monostearate, and sodium stearoyl lactylate,
   silicone wax,
   quaternary ammonium chlorides,
   an encapsulated oil,
   microcapsule mineral oil,
   butyleneglycol,
   and mixtures thereof.

9. The alcohol disinfecting composition according to claim 1 wherein the foam stabilizing agent is selected from the group consisting of 2-butoxyethanol, glycerine butyleneglycol, cetrimonium chloride, behentrimonium chloride, and combinations thereof.

10. The alcohol disinfecting composition according to claim 1 wherein any one of the moisturizer, emollient and combinations thereof is selected from the group consisting of
    lanolin,
    vinyl alcohol,
    polyvinyl pyrrolidone,
    polyols selected from the group consisting of glycerol, propylene glycol, butyleneglycol and sorbitol,
    a fatty alcohol selected from the group consisting of cetyl alcohol, stearyl alcohol, lauryl alcohol, myristyl alcohol and palmityl alcohol,
    ceteareth 20,
    an alkylglucoside,
    and combinations thereof.

11. The alcohol disinfecting composition according to claim 1 wherein the moisturizer or emollient are selected from the group consisting of glyceryl oleate, glycerine, cocoglucoside, PEG-200 hydrogenated glyceryl palmate, or dihydroxypropyl PEG-5 linoleammonium chloride, PEG-7 glyceryl cocoate, and combinations thereof.

12. The alcohol disinfecting composition according to claim 1 further including a preservative in an amount from about 0.01 to about 5% by weight of the total composition.

13. The alcohol disinfecting composition according to claim 1 further comprising an acid or a base to adjust a pH of the disinfecting composition to a pre-selected pH present in an amount from about 0.05 to about 0.5% by weight of the total composition.

14. The alcohol disinfecting composition according to claim 13 wherein the acid is selected from the group consisting of hydrochloric acid, citric acid and phosphoric acid, and the base is sodium sesquicarbonate.

15. The alcohol disinfecting composition according to claim 1 wherein the composition is stored in an unpressurized dispenser having a dispenser pump for mixing the disinfecting composition with air and dispensing foam therefrom.

16. The alcohol disinfecting composition according to claim 1 wherein one or more of the moisturizers, emollients, lipid layer enhancers, or combinations thereof is selected from the group consisting of
    lanolin,
    vinyl alcohol,
    polyvinyl pyrrolidone,
    polyols selected from the group consisting of glycerol, propylene glycol, butyleneglycol and sorbitol,
    a fatty alcohol selected from the group consisting of cetyl alcohol, stearyl alcohol, lauryl alcohol, myristyl alcohol and palmityl alcohol,
    ceteareth 20,
    an alkylglucoside,
    mixtures of alkylglucoside and glyceryl oleate,
    PEG-200 hydrogenated glyceryl palmate,
    dihydroxypropyl PEG-5 linoleammonium chloride,
    PEG-7 glyceryl cocoate,
    and combinations thereof.

17. The alcohol disinfecting composition according to claim 1 further comprising other constituents or materials including organic gums and colloids, lower alkanolamides of higher fatty acids, short chain diols and/or triols, fragrance, coloring matter, ultraviolet absorbers, solvents, emulsifiers, buffers, conditioning agents, antioxidants, bactericides, or medicinal active ingredients.

18. A method of forming a foam using a composition according to claim 1, by storing said composition in a container and having a dispenser pump activating the dispenser pump to mix the alcohol and silicone-based surface active agent mixture with air under low pressure to form a low pressure foam containing alcohol which is dispensed from said dispenser.

19. The composition according to claim 1 wherein the silicone-based surfactant is a Bis-PEG-[10-20] dimethicone.

20. The composition according to claim 19 wherein the foam stabilizing agent is selected from the group consisting of cationic emulsifiers and quaternary ammonium compounds.

21. The composition according to claim 19 wherein the foam stabilizing agent is selected from the group consisting of 2-butoxyethanol, glycerine, butyleneglycol, cetrimonium chloride, and behentrimonium chloride.

22. The composition according to claim 1 wherein the foam stabilizing agent is behentrimonium chloride.

23. The composition according to claim 19 further comprising cocoglucoside and glyceryl oleate.

24. The composition according to claim 22 further comprising
   PEG-200 hydrogenated glyceryl palmate,
   PEG-7 glyceryl cocoate, and
   dihydroxypropyl PEG-5 linoleammonium chloride.

25. The composition according to claim 23 further comprising n-propanol.

* * * * *